(12) United States Patent
Singh et al.

(10) Patent No.: US 10,324,088 B2
(45) Date of Patent: Jun. 18, 2019

(54) METHODS FOR ESTABLISHING A VEDOLIZUMAB DOSING REGIMEN TO TREAT PATIENTS WITH IRRITABLE BOWEL DISEASE

(71) Applicant: Nestec S.A., Vevey (CH)

(72) Inventors: Sharat Singh, San Diego, CA (US); Anjali Jain, San Diego, CA (US); Venkateswarlu Kondragunta, San Diego, CA (US)

(73) Assignee: NESTEC S.A., Vevey (CH)

( * ) Notice: Subject to any disclaimer, the term of this patent is extended or adjusted under 35 U.S.C. 154(b) by 0 days.

(21) Appl. No.: 15/601,921

(22) Filed: May 22, 2017

(65) Prior Publication Data

US 2017/0254806 A1 Sep. 7, 2017

Related U.S. Application Data

(63) Continuation of application No. PCT/IB2015/059303, filed on Dec. 2, 2015.

(60) Provisional application No. 62/086,549, filed on Dec. 2, 2014, provisional application No. 62/157,903, filed on May 6, 2015.

(51) Int. Cl.
| | |
|---|---|
| *A61K 39/395* | (2006.01) |
| *A61K 39/00* | (2006.01) |
| *G01N 33/564* | (2006.01) |
| *G01N 33/68* | (2006.01) |
| *G01N 33/15* | (2006.01) |
| *G01N 33/48* | (2006.01) |

(52) U.S. Cl.
CPC .......... *G01N 33/564* (2013.01); *G01N 33/15* (2013.01); *G01N 33/48* (2013.01); *G01N 33/68* (2013.01); *G01N 2333/70546* (2013.01); *G01N 2800/065* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,873,742 B2 * | 1/2018 | Keir | G01N 33/6893 |
| 2013/0337470 A1 * | 12/2013 | Chackerian | G01N 33/566 |
| | | | 435/7.21 |

FOREIGN PATENT DOCUMENTS

| | | |
|---|---|---|
| WO | 2009/140684 A2 | 11/2009 |
| WO | 2012/061074 A1 | 5/2012 |
| WO | 2014/055824 A1 | 4/2014 |

OTHER PUBLICATIONS https://www.biocompare.com/pfu/110447/soids/21192/Antibodies/Integrin_alpha_4_beta_7, downloaded Aug. 23, 2018). (Year: 2018).*
Rosario, M. et al., "P488 Exposure-response relationship of vedolizumab after 6 weeks of treatment in adults with Crohn's disease," Journal of Crohn's and Colitis, 8:S270, Feb. 1, 2014.
Rosario, M. et al., "P489 Exposure-response relationship during vedolizumab induction therapy in adults with ulcerative colitis," Journal of Crohn's and Colitis, 8:S270-S271, Feb. 1, 2014.
Sandborn, W. et al., "Vedolizumab as induction and maintenance therapy for Crohn's disease," New England Journal of Medicine, 369(8):711-721, 2013.
Smith, M. et al., "Vedolizumab: An a alpha(4)beta(7) integrin inhibitor for inflammatory bowel diseases," Annals of Pharmacotherapy, 48(12):1629-35, 2014.

* cited by examiner

*Primary Examiner* — Shulamith H Shafer
(74) *Attorney, Agent, or Firm* — Kilpatrick Townsend & Stockton LLP

(57) ABSTRACT

The present invention provides methods for predicting whether an individual having inflammatory bowel disease (IBD) is likely to respond to vedolizumab treatment. Also provided are methods for predicting whether an individual with IBD such as Crohn's disease or ulcerative colitis will develop autoantibodies against vedolizumab. The present invention also provides a treatment regimen for an IBD patient which includes measuring the level of one or more predictive markers of response to vedolizumab prior to administering the anti-α4β7 integrin drug.

9 Claims, 22 Drawing Sheets

Higher TNFa levels at baseline result in lower vedolizumab at week 6

Higher VEGF levels at baseline result in lower vedolizumab at week 6

Higher ANG-2 levels at baseline result in lower vedolizumab at week 6

Higher ANG-1 levels at baseline result in higher vedolizumab at week 6

Higher ADA levels at baseline result in Higher vedolizumab at week 6

Higher ADA levels at week 2 result in Higher vedolizumab at week 6

Higher human serum albumin levels at baseline result in higher vedolizumab at week 6

Association between levels of vedolizumab at week 6 and baseline HGB (Hemoglobin): No association Association between level of vedolizumab at week 6 and level of IL-12p40 at baseline (increased levels)

Association between levels of vedolizumab at week 6 and levels of MMP9 at week 2 (increased levels)

Association between vedolizumab at wk 6 and MadCAM-1 at week 2

Association between Vedolizumab at week 6 and CRP at baseline

Multiple regression model with interaction between VCAM and α4β7 integrin (baseline) to predict vedolizumab at week 6.

Multiple regression model with interaction between VCAM and MAdCAM-1 (baseline) to predict vedolizumab at week 6.

Baseline MadCAM-1 negatively correlated with ICAM-1 (-0.4564: p-value=0.21)

MadCAM-1 at baseline is negatively correlated to VCAM-1 at baseline (-0.5459, p-value=0.1284)

MadCam expression decreases with Vedo treatment

Human serum abumin at baseline

Human serum abumin at baseline

METHODS FOR ESTABLISHING A VEDOLIZUMAB DOSING REGIMEN TO TREAT PATIENTS WITH IRRITABLE BOWEL DISEASE

CROSS-REFERENCE TO RELATED APPLICATIONS

The present application is a continuation of PCT/IB2015/059303, filed Dec. 2, 2015, which claims priority to U.S. Provisional Application Nos. 62/086,549, filed Dec. 2, 2014 and 62/157,903, filed May 6, 2015, the contents of which are hereby incorporated by reference in their entireties for all purposes.

BACKGROUND OF THE INVENTION

Inflammatory bowel disease (IBD), which occurs worldwide and afflicts millions of people, is the collective term used to describe three gastrointestinal disorders of unknown etiology: Crohn's disease (CD), ulcerative colitis (UC), and indeterminate colitis (IC). IBD, together with irritable bowel syndrome (IBS), will affect one-half of all Americans during their lifetime, at a cost of greater than $2.6 billion dollars for IBD and greater than $8 billion dollars for IBS. A primary determinant of these high medical costs is the difficulty of diagnosing digestive diseases and how these diseases will progress. The cost of IBD and IBS is compounded by lost productivity, with people suffering from these disorders missing at least 8 more days of work annually than the national average.

Despite the successes of anti-TNF$\alpha$ therapies in the treatment of IBD, a subpopulation of patients are refractory to treatment, highlighting an unmet medical need for new therapies. Vedolizumab is a gut-specific, $\alpha 4\beta 7$ integrin-neutralizing monoclonal Ab, which does not affect peripheral blood cell counts and appears to lack systemic effects. Vedolizumab is a new anti-inflammatory treatment option for the management of therapy-refractory patients.

There is a need in the art for methods of therapeutic management of diseases such as ulcerative colitis and Crohn's Disease using an individualized approach to monitor drug efficacy and optimize therapy accordingly. The methods need to include assessing disease course and clinical parameters such as pharmacodynamics, disease activity indices, disease burden, and inflammatory biomarkers. There is a need to predict whether a patient will respond to vedolizumab therapy. The present invention satisfies this and other needs.

BRIEF SUMMARY OF THE INVENTION

The present invention provides methods for predicting whether a subject having inflammatory bowel disease (IBD) will respond to anti-$\alpha 4\beta 7$ integrin drug treatment. The method comprises: (a) detecting the presence or level of at least one predictive marker selected from the group consisting of TNF$\alpha$, human serum albumin (HSA), VEGF, angiopoietin-1 (ANG-1), angiopoietin-2 (ANG-2), adenosine deaminase (ADA), serum $\alpha 4\beta 7$ integrin, IL-12p40, C-reactive protein (CRP), matrix metalloproteinase 9 (MMP9), MAdCAM-1, VCAM-1, ICAM-1, or a combination thereof in a sample from the subject; and (b) classifying the subject as a responder or a non-responder to the anti-$\alpha 4\beta 7$ integrin drug treatment according to a predictive marker profile based on a higher or lower level of the at least one predictive marker compared to a corresponding reference value. In some embodiments, classifying comprises applying a statistical analysis to the predictive marker profile to determine if the subject is a responder or a non-responder to the anti-$\alpha 4\beta 7$ integrin drug treatment. In some embodiments, the at least one predictive marker comprises at least 1, 2, 3, 4, 5, 6, 7, 8, 9, 10, 11, 12, 13 or more predictive markers. In some embodiments, the inflammatory bowel disease is ulcerative colitis (UC) or Crohn's Disease (CD).

In some embodiments, the subject is classified as a responder if the level of ANG-1, ADA, HSA, IL-12p40, MMP9, ICAM-1, and/or serum $\alpha 4\beta 7$ integrin is higher than the corresponding reference value. In some instances, the subject is classified as a responder if the level of MadCAM-1, VCAM-1 and/or TNF$\alpha$ is lower than the corresponding reference value. In other embodiments, the subject is classified as a non-responder if the level of TNF$\alpha$, VEGF, ANG-2, CRP, and/or VCAM-1 is higher than the corresponding reference value.

In some embodiments, detecting the presence or level of the at least one predictive marker comprises performing a proximity dual detection assay or an immunoassay. In some cases, the proximity dual detection assay is a Collaborative Enzyme Enhanced Reactive Immunoassay (CEER™).

In some embodiments, the anti-$\alpha 4\beta 7$ integrin drug is ENTYVIO® (vedolizumab).

In some embodiments, the sample is selected from the group consisting of a whole blood, serum or plasma sample.

In some embodiments, the subject has had an inadequate response with, has lost response to, or was intolerant to an anti-TNF$\alpha$ drug. The anti-TNF$\alpha$ drug can be a member selected from the group consisting of REMICADE® (infliximab), ENBREL® (etanercept), HUMIRA® (adalimumab), CIMZIA® (certolizumab pegol), SIMPONI® (golimumab), STELARA® (ustekinumab), and combinations thereof. In other embodiments, the subject has not previously been administered an anti-$\alpha 4\beta 7$ integrin drug.

In some instances, the method further comprises applying a statistical analysis to the predictive marker profile to predict whether the subject will develop autoantibodies against an anti-$\alpha 4\beta 7$ integrin drug.

Also provided herein is a method for predicting whether a subject having inflammatory bowel disease (IBD) is likely to develop autoantibodies against an anti-$\alpha 4\beta 7$ integrin drug. The method comprises (a) detecting the presence or level of at least one predictive marker selected from the group consisting of TNF$\alpha$, human serum albumin (HSA), VEGF, angiopoietin-1 (ANG-1), angiopoietin-2 (ANG-2), adenosine deaminase (ADA), serum $\alpha 4\beta 7$ integrin, IL-12p40, C-reactive protein (CRP), MMP9, MAdCAM-1, VCAM-1, ICAM-1, and a combination thereof in a sample from the subject; and (b) applying a statistical analysis to the presence or level of the at least one predictive marker of step (a) to generate a predictive marker profile to determine whether the subject is likely to develop or not to develop autoantibodies against the anti-$\alpha 4\beta 7$ integrin drug. In one embodiment, the method further comprises determining the presence or level of anti-drug antibodies in the sample from the subject. In some embodiments, the anti-$\alpha 4\beta 7$ integrin drug is ENTYVIO® (vedolizumab).

In some embodiments, the inflammatory bowel disease is ulcerative colitis (UC) or Crohn's Disease (CD).

The at least one predictive marker can include at least 1, 2, 3, 4, 5, 6, 7, 8, 9, 10, 11, 12, 13 or more predictive markers. In some embodiments, detecting the presence or level of at least one predictive marker comprises performing a proximity dual detection assay or an immunoassay. In one embodiment, the proximity dual detection assay is a Collaborative Enzyme Enhanced Reactive Immunoassay (CEER™).

In some embodiments, the subject is likely not to develop autoantibodies if the level of ANG-1, ADA, HSA, IL-12p40, MMP9, ICAM-1, and/or serum α4β7 integrin is higher than the corresponding reference value. In other embodiments, the subject is likely not to develop autoantibodies if the level of MadCAM-1, VCAM-1 and/or TNFα is lower than the corresponding reference value. In other embodiments, the subject is likely to develop autoantibodies if the level of TNFα, VEGF, ANG-2, CRP, and/or VCAM-1 is higher than the corresponding reference value.

In some embodiments, the subject has been previously administered the anti-α4β7 integrin drug. In some cases, the subject has not been administered the anti-α4β7 integrin drug.

In some embodiments, the subject is maintained or is recommended to be maintained on the anti-α4β7 integrin drug if the subject is likely not to develop autoantibodies. The subject may be administered the anti-α4β7 integrin drug.

In other embodiments, the subject is not maintained or is recommended not to be maintained on the anti-α4β7 integrin drug if the subject is likely to develop autoantibodies. The subject may not be administered the anti-α4β7 integrin drug.

In some embodiments, the sample is selected from the group consisting of a whole blood, serum or plasma sample.

In some embodiments, the anti-α4β7 integrin drug is ENTYVIO® (vedolizumab).

In some embodiments, the subject has had an inadequate response with, has lost response to, or is intolerant to an anti-TNFα drug. The anti-TNFα drug may be a member selected from the group consisting of REMICADE® (infliximab), ENBREL® (etanercept), HUMIRA® (adalimumab), CIMZIA® (certolizumab pegol), SIMPONI® (golimumab), STELARA® (ustekinumab), and combinations thereof.

The present invention also provides a method for predicting whether a subject having inflammatory bowel disease (IBD) will develop autoantibodies against an anti-α4β7 integrin drug at a later time point during a course of therapy with the anti-α4β7 integrin drug. The method includes (a) measuring the presence or level of at least one predictive marker at a first time point in a sample from the subject to determine a first predictive marker profile, wherein the at least one predictive marker is selected from the group consisting of TNFα, human serum albumin (HSA), VEGF, angiopoietin-1 (ANG-1), angiopoietin-2 (ANG-2), adenosine deaminase (ADA), serum α4β7 integrin, IL-12p40, C-reactive protein (CRP), MMP9, MAdCAM-1, VCAM-1, ICAM-1, and a combination thereof; (b) measuring the presence of level of the same at least one predictive marker at a later time point in a second sample from the subject to determine a second predictive marker profile; and (c) applying a statistical analysis to the first and second predictive marker profiles to determine that the subject will develop autoantibodies to the anti-α4β7 integrin drug during the course of therapy.

In some embodiments, the at least one predictive marker comprises at least 1, 2, 3, 4, 5, 6, 7, 8, 9, 10, 11, 12, 13, or more predictive markers.

In some embodiments, detecting the presence or level of at least one predictive marker comprises performing a proximity dual detection assay or an immunoassay. In some instances, the proximity dual detection assay is a Collaborative Enzyme Enhanced Reactive Immunoassay (CEER™).

In some embodiments, the anti-α4β7 integrin drug is ENTYVIO® (vedolizumab).

In some embodiments, the later time point is at weeks 2, 4, 6, 8, 10, 12, 16, 24, 32, 40, 48, or 52 during the course of therapy.

Provided herein is a method for inducing clinical remission in a subject having inflammatory bowel disease (IBD) and after receiving an induction therapy of an anti-α4β7 integrin drug. The method comprises administering a maintenance therapy of an anti-α4β7 integrin drug to a subject with IBD and having a higher level of serum α4β7 integrin and a lower level of MadCAM-1 compared to corresponding levels at baseline. In some embodiments, clinical remission corresponds to a score on the Crohn's Disease Activity Index (CDAI) of less than or equal to 150. The maintenance therapy can include administering a dose of about 300 mg of the anti-α4β7 integrin drug, e.g., vedolizumab every 8 weeks during the course of therapy. Alternatively, the maintenance therapy includes administering a dose of about 300 mg of ENTYVIO® (vedolizumab) every 4 weeks of the regimen.

Also provided herein is a method for inducing a clinical response in a subject having inflammatory bowel disease (IBD), comprising administering an induction therapy of an anti-α4β7 integrin drug to a subject with IBD and having a higher level of ANG-1, ADA, HSA, IL-12p40, MMP9, ICAM-1, and/or serum α4β7 integrin, and/or a lower level of MadCAM-1, VCAM-1, and/or TNFα compared to a corresponding reference value. In some embodiments, the induction therapy comprises administering a dose of about 300 mg of the anti-α4β7 integrin drug, e.g., vedolizumab at weeks 0, 2 and 6 during the course of therapy. In some embodiments, clinical response corresponds to a 70-point or greater decrease in CDAI score. In other embodiments, clinical response in a subject with CD corresponds to a 100-point or more decrease in CDAI score. In some embodiments, clinical response in a subject with UC corresponds to a reduction in the Mayo Clinical score of at least 3 points and a decrease of at least 30% from the baseline score, with a decrease of at least 1 point on the rectal bleeding score of 0 or 1 for UC.

The present invention provides a therapy regimen for an anti-α4β7 integrin drug, the therapy regimen comprising measuring the presence or level of at least one predictive marker selected from the group consisting of TNFα, human serum albumin (HSA), VEGF, angiopoietin-1 (ANG-1), angiopoietin-2 (ANG-2), adenosine deaminase (ADA), serum α4β7 integrin, IL-12p40, C-reactive protein (CRP), MMP9, MAdCAM-1, VCAM-1, ICAM-1, and a combination thereof in a sample from the subject; and administering the therapy regimen of the anti-α4β7 integrin drug according to a predictive marker profile based on a higher or lower level of the at least one predictive marker compared to a corresponding reference value.

In some embodiments, the therapy regimen of the anti-α4β7 integrin drug is administered if the level of MadCAM-1 and/or TNFα is lower than the corresponding reference value. In other embodiments, the therapy regimen is not administered if the level of TNFα, VEGF, ANG-2, CRP, and/or VCAM-1 is higher than the corresponding reference value. In some instances, the therapy regimen is an induction therapy regimen. For instance, an induction therapy regimen for ENTYVIO® (vedolizumab) comprises administering a dose of about 300 mg of the anti-α4β7 integrin drug at weeks 0, 2 and 6 of the regimen.

In some embodiments, the therapy regimen of the anti-α4β7 integrin drug is administered if the level of MadCAM-1 is lower and/or the level of serum α4β7 integrin is higher than the corresponding reference value. In some instances, the therapy regimen is a maintenance therapy regimen. For instance, a maintenance therapy regimen for ENTYVIO® (vedolizumab) comprises administering a dose of about 300 mg of the anti-α4β7 integrin drug every 8 weeks of the regimen. In other cases, the maintenance therapy regimen for ENTYVIO® (vedolizumab) includes administering a dose of about 300 mg of the anti-α4β7 integrin drug every 4 weeks of the regimen.

These and other aspects, objects, embodiments will become more apparent when read with the detailed description and figures that follow.

BRIEF DESCRIPTION OF THE DRAWINGS

FIG. 1A shows a diagram of an exemplary embodiment of the present invention that shows higher TNFα levels at baseline result in lower vedolizumab at week 6.

FIG. 1B shows a diagram of an exemplary embodiment of the present invention that shows higher TNFα levels at week 2 result in lower vedolizumab at week 6.

FIG. 3A shows a diagram of an exemplary embodiment of the present invention that shows higher ANG-2 levels at baseline result in lower vedolizumab at week 6. FIG. 3B shows a diagram of an exemplary embodiment of the present invention that shows higher higher ANG-1 levels at baseline result in higher vedolizumab at week 6.

FIG. 4A shows a diagram of an exemplary embodiment of the present invention that shows higher ADA levels at baseline result in higher vedolizumab at week 6. FIG. 4B shows a diagram of an exemplary embodiment of the present invention that shows higher ADA levels at week 2 result in higher vedolizumab at week 6.

FIG. 5A shows higher albumin levels at baseline result in higher vedolizumab at week 6. FIG. 5B shows a lack of association between vedolizumab at week 6 and hemoglobin (HGB) at baseline.

FIG. 6A shows a positive association between vedolizumab at week 6 and IL-12p40 levels at baseline. FIG. 6B shows a positive association between vedolizumab at week 6 and MMP9 levels at week 2.

FIG. 11A represent VCAM-1 and α4β7 integrin at baseline to predict vedolizumab levels at week 6. FIG. 11B shows multiple regression model with interaction between VCAM-1 and MAdCAM-1 (baseline) to predict vedolizumab at week 6.

FIG. 12A shows that baseline MAdCAM-1 levels are negatively correlated with soluble ICAM-1 levels. FIG. 12B shows a negative correlation between MAdCAM-1 at baseline and soluble VCAM-1 at baseline.

FIG. 19A shows that higher levels of serum albumin at baseline are associated with higher levels of vedolizumab at week 6. FIG. 19B shows that higher levels of serum albumin at baseline are associated with higher levels of vedolizumab at week 14.

FIG. 20A shows that lower levels of TNFα (at baseline) are associated with higher levels of vedolizumab at week 2. FIG. 20B shows that higher levels of TNFα at baseline are associated with lower levels of vedolizumab at week 6.

DETAILED DESCRIPTION OF THE INVENTION

I. Definitions

Figure 1A:
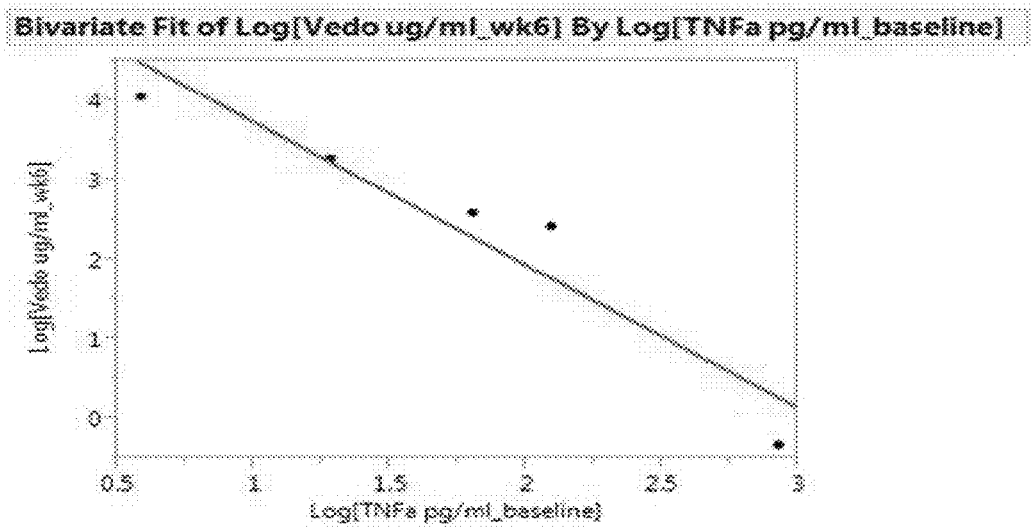
FIGS. 1A and 1B depict the associated between TNFα levels and vedolizumab in patient with CD or UC.

The term "inflammatory bowel disease" or "IBD" includes gastrointestinal disorders such as, e.g., Crohn's disease (CD), ulcerative colitis (UC), and indeterminate colitis (IC). Inflammatory bowel diseases (e.g., CD, UC, and IC) are distinguished from all other disorders, syndromes, and abnormalities of the gastroenterological tract, including irritable bowel syndrome (IBS).

The term "sample" as used herein includes any biological specimen obtained from a patient. Samples include, without limitation, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy of a site of inflammation (e.g., needle biopsy), and cellular extracts thereof. In some embodiments, the sample is whole blood or a fractional component thereof such as plasma, serum, or a cell pellet. In other embodiments, the sample is obtained by isolating PBMCs and/or PMN cells using any technique known in the art. In yet other embodiments, the sample is a tissue biopsy, e.g., from a site of inflammation such as a portion of the gastrointestinal tract or synovial tissue.

The term "marker" or "biomarker" includes any biochemical marker, serological marker, genetic marker, or other clinical or echographic characteristic that can be used predicting whether a subject having inflammatory bowel disease (IBD) will respond to vedolizumab treatment. The marker can be used to classify a sample from the subject is a responder or a non-responder to vedolizumab therapy. In some embodiments, the markers are utilized in combination with a statistical analysis to provide a prognosis of IBD in an individual.

The term "classifying" includes "to associate" or "to categorize" a sample with a disease state. In certain instances, "classifying" is based on statistical evidence, empirical evidence, or both. In certain embodiments, the methods and systems of classifying use a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The present invention relies, in part, on determining the presence (or absence) or level (e.g., concentration) of at least one marker in a sample obtained from an individual. As used herein, the term "detecting the presence of at least one marker" includes determining the presence of each marker of interest by using any quantitative or qualitative assay known to one of skill in the art. In certain instances, qualitative assays that determine the presence or absence of a particular trait, variable, genotype, and/or biochemical or serological substance (e.g., protein or antibody) are suitable for detecting each marker of interest. In certain other instances, quantitative assays that determine the presence or absence of DNA, RNA, protein, antibody, or activity are suitable for detecting each marker of interest. As used herein, the term "detecting the level of at least one marker" includes determining the level of each marker of interest by using any direct or indirect quantitative assay known to one of skill in the art. In certain instances, quantitative assays that determine, for example, the relative or absolute amount of DNA, RNA, protein, antibody, or activity are suitable for detecting the level of each marker of interest. One skilled in the art will appreciate that any assay useful for detecting the level of a marker is also useful for detecting the presence or absence of the marker.

The term "predictive profile" includes 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, or more marker(s) of an individual, wherein the marker(s) can be a serological marker, a protein marker, a genetic marker, and the like. In some embodiments, the marker profile together with a statistical analysis can provide physicians and caregivers valuable diagnostic insight. In other embodiments, the marker profile with optionally a statistical analysis provides a projected disease condition (e.g., IBD or CD). By using multiple markers (e.g., serological, inflammation, protein, etc.) in conjunction with statistical analyses, the assays described herein provide diagnostic, prognostic and therapeutic value by identifying patients with IBD or a clinical subtype thereof, predicting risk of developing complicated disease, assisting in assessing the rate of disease progression (e.g., rate of progression to complicated disease or surgery), and assisting in the selection of therapy.

The term "individual," "subject," or "patient" typically refers to humans, but also to other animals including, e.g., other primates, rodents, canines, felines, equines, ovines, porcines, and the like.

The term "prognosis" includes a prediction of the probable course and outcome of UC or CD or the likelihood of recovery from the disease.

The term "monitoring the progression or regression of UC or CD" includes the use of the methods of the present invention to determine the disease state (e.g., severity of UC) of an individual. In some aspects, the methods of the present invention can also be used to predict the progression of UC or CD, e.g., by determining a likelihood for UC to progress either rapidly or slowly in an individual based on the presence or level of at least one marker in a sample. In other aspects, the methods of the present invention can also be used to predict the regression of UC, e.g., by determining a likelihood for UC to regress either rapidly or slowly in an individual based on the presence or level of at least one marker in a sample.

The term "course of therapy" includes any therapeutic approach taken to relieve or prevent one or more symptoms associated with UC or CD. The term encompasses administering any compound, drug, procedure, or regimen useful for improving the health of an individual with UC and includes any of the therapeutic agents as well as surgery. One skilled in the art will appreciate that either the course of therapy or the dose of the current course of therapy can be changed, e.g., based upon the methods of the present invention.

The phrase "determining the course of therapy" and the like includes the use of an empirically derived index, score or analysis to select for example, selecting a dose of drug, selecting an appropriate drug, or a course or length of therapy, a therapy regimen, or maintenance of an existing drug or dose. In certain aspects, a derived or measured index can be used to determine the course of therapy.

As used herein, the phrase "at a later time point" includes phrases such as "by a later time point" and "within the later time point." For example, a method for predicting whether a subject will develop autoantibodies to an anti-α4β7 integrin drug (e.g., vedolizumab) at a later time point during a course of therapy includes a method for predicting whether a subject will develop autoantibodies to an anti-α4β7 integrin drug by the later time point during the course of therapy as well as a method for predicting whether a subject will develop autoantibodies to an anti-α4β7 integrin drug within the later time point during the course of therapy.

In "quartile analysis", there are three numbers (values) that divide a range of data into four equal parts. The first quartile (also called the 'lower quartile') is the number below which lies the bottom 25 percent of the data. The second quartile (the 'median') divides the range in the middle and has 50 percent of the data below it. The third quartile (also called the 'upper quartile') has 75 percent of the data below it and the top 25 percent of the data above it. As a non-limiting example, quartile analysis can be applied to the concentration level of a marker such as an antibody or other protein marker described herein, such that a marker level in the first quartile (<25%) is assigned a value of 1, a marker level in the second quartile (25-50%) is assigned a value of 2, a marker level in the third quartile (51%-<75%) is assigned a value of 3, and a marker level in the fourth quartile (75%-100%) is assigned a value of 4.

II. Detailed Description of the Embodiments

The present invention provides methods for predicting whether a subject having inflammatory bowel disease (IBD) will respond to vedolizumab treatment, the method comprises:
  (a) determining a predictive marker profile by detecting the presence or level of at least one predictive marker in a sample from a subject; and
  (b) classifying the sample as either a responder or a non-responder to vedolizumab therapy.

The present invention also provides methods for predicting whether a subject having inflammatory bowel disease (IBD) will develop anti-drug antibodies (autoantibodies) against an anti-α4β7 integrin drug (e.g., vedolizumab), the method comprises:
  (a) determining a predictive marker profile by detecting the presence or level of at least one predictive marker in a sample from a subject; and
  (b) applying a statistical analysis to the predictive marker profile to determine that the subject is likely to develop or not develop anti-drug antibodies.

Additionally, the present invention also provides methods for predicting whether a subject having inflammatory bowel disease (IBD) will develop anti-drug antibodies (autoantibodies) against an anti-α4β7 integrin drug (e.g., vedolizumab) at a later time point during a course of therapy with the anti-α4β7 integrin drug, the method comprises:
  (a) measuring the presence or level of at least one predictive marker at a first time point in a sample from the subject to determine a first predictive marker profile;
  (b) measuring the presence or level of the same at least one predictive marker at a later time point in a sample from the subject to determine a second predictive marker profile; and
  (c) applying a statistical analysis to the first and second predictive marker profiles to determine that the subject will develop autoantibodies to the anti-α4β7 integrin drug, during the course of therapy.

In certain aspects, vedolizumab (ENTYVIO®) is indicated in adult patients with moderately to severely active ulcerative colitis (UC) or Crohn's Disease (CD) who have had an inadequate response with, lost response to, or were intolerant to a tumor necrosis factor (TNF) therapy, or had an inadequate response with, were intolerant to, or demonstrated dependence on corticosteroids for inducing and maintaining clinical response, inducing and maintaining clinical remission, improving endoscopic appearance of the mucosa, and achieving corticosteroid-free remission.

Vedolizumab can be administered as an intravenous infusion over 30 minutes. The recommended dosage of in adults with ulcerative colitis or Crohn's disease is 300 mg administered by intravenous infusion at zero, two and six weeks (0, 2, and 6 as induction therapy) and then every eight weeks thereafter (14 weeks, 22 weeks, etc. as maintenance therapy). Alternatively, the maintenance therapy may include administering vedolizumab every 4 weeks. Therapy may be discontinued in patients who show no evidence of therapeutic benefit by week 14.

A. Inflammatory Bowel Disease (IBD)

Inflammatory bowel disease (IBD) is a group of inflammatory conditions of the large intestine and small intestine. The main forms of IBD are Crohn's disease (CD) and ulcerative colitis (UC). Other less common forms of IBD include, e.g., indeterminate colitis (IC), collagenous colitis, lymphocytic colitis, ischemic colitis, diversion colitis, Behçet's syndrome, infective colitis, and the like. U.S. Patent Publication 2008/0131439, entitled "Methods of Diagnosing Inflammatory Bowel Disease" is incorporated herein by reference for all purposes.

1. Crohn's Disease

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity.

The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel. CD also includes complications such as inflammation of the eye, joints, and skin, liver disease, kidney stones, and amyloidosis. In addition, CD is associated with an increased risk of intestinal cancer.

Several features are characteristic of the pathology of CD. The inflammation associated with CD, known as transmural inflammation, involves all layers of the bowel wall. Thickening and edema, for example, typically also appear throughout the bowel wall, with fibrosis present in long-standing forms of the disease. The inflammation characteristic of CD is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display typical discrete granulomas, while others show a diffuse granulomatous reaction or a nonspecific transmural inflammation. As a result, the presence of discrete granulomas is indicative of CD, although the absence of granulomas is also consistent with the disease. Thus, transmural or discontinuous inflammation, rather than the presence of granulomas, is a preferred diagnostic indicator of CD (Rubin and Farber, Pathology (Second Edition), Philadelphia, J.B. Lippincott Company (1994)).

Crohn's disease may be categorized by the behavior of disease as it progresses. This was formalized in the Vienna classification of Crohn's disease. See, Gasche et al., *Inflamm. Bowel Dis.,* 6:8-15 (2000). There are three categories of disease presentation in Crohn's disease: (1) stricturing, (2) penetrating, and (3) inflammatory. Stricturing disease causes narrowing of the bowel which may lead to bowel obstruction or changes in the caliber of the feces. Penetrating disease creates abnormal passageways (fistulae) between the bowel and other structures such as the skin. Inflammatory disease (also known as non-stricturing, non-penetrating disease) causes inflammation without causing strictures or fistulae.

As such, Crohn's disease represents a number of heterogeneous disease subtypes that affect the gastrointestinal tract and may produce similar symptoms. As used herein in reference to CD, the term "clinical subtype" includes a classification of CD defined by a set of clinical criteria that distinguish one classification of CD from another. As non-limiting examples, subjects with CD can be classified as having stricturing (e.g., internal stricturing), penetrating (e.g., internal penetrating), or inflammatory disease as described herein, or these subjects can additionally or alternatively be classified as having fibrostenotic disease, small bowel disease, internal perforating disease, perianal fistulizing disease, UC-like disease, the need for small bowel surgery, the absence of features of UC, or combinations thereof.

In certain instances, subjects with CD can be classified as having complicated CD, which is a clinical subtype characterized by stricturing or penetrating phenotypes. In certain other instances, subjects with CD can be classified as having a form of CD characterized by one or more of the following complications: fibrostenosis, internal perforating disease, and the need for small bowel surgery. In further instances, subjects with CD can be classified as having an aggressive form of fibrostenotic disease requiring small bowel surgery. Criteria relating to these subtypes have been described, for example, in Gasche et al., *Inflamm. Bowel Dis.,* 6:8-15 (2000); Abreu et al., *Gastroenterology,* 123:679-688 (2002); Vasiliauskas et al., *Gut,* 47:487-496 (2000); Vasiliauskas et al., *Gastroenterology,* 110:1810-1819 (1996); and Greenstein et al., *Gut,* 29:588-592 (1988).

The "fibrostenotic subtype" of CD is a classification of CD characterized by one or more accepted characteristics of fibrostenosing disease. Such characteristics of fibrostenosing disease include, but are not limited to, documented persistent intestinal obstruction or an intestinal resection for an intestinal obstruction. The fibrostenotic subtype of CD can be accompanied by other symptoms such as perforations, abscesses, or fistulae, and can further be characterized by persistent symptoms of intestinal blockage such as nausea, vomiting, abdominal distention, and inability to eat solid food. Intestinal X-rays of patients with the fibrostenotic subtype of CD can show, for example, distention of the bowel before the point of blockage.

The requirement for small bowel surgery in a subject with the fibrostenotic subtype of CD can indicate a more aggressive form of this subtype. Additional subtypes of CD are also known in the art and can be identified using defined clinical criteria. For example, internal perforating disease is a clinical subtype of CD defined by current or previous evidence of entero-enteric or entero-vesicular fistulae, intra-abdominal abscesses, or small bowel perforation. Perianal perforating disease is a clinical subtype of CD defined by current or previous evidence of either perianal fistulae or abscesses or rectovaginal fistula. The UC-like clinical subtype of CD can be defined by current or previous evidence of left-sided colonic involvement, symptoms of bleeding or urgency, and crypt abscesses on colonic biopsies. Disease location can be classified based on one or more endoscopic, radiologic, or pathologic studies.

One skilled in the art understands that overlap can exist between clinical subtypes of CD and that a subject having CD can have more than one clinical subtype of CD. For example, a subject having CD can have the fibrostenotic subtype of CD and can also meet clinical criteria for a clinical subtype characterized by the need for small bowel surgery or the internal perforating disease subtype. Similarly, the markers described herein can be associated with more than one clinical subtype of CD.

2. Ulcerative Colitis

Ulcerative colitis (UC) is a disease of the large intestine characterized by chronic diarrhea with cramping, abdominal pain, rectal bleeding, loose discharges of blood, pus, and mucus. The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

UC is a diffuse disease that usually extends from the most distal part of the rectum for a variable distance proximally. The term "left-sided colitis" describes an inflammation that involves the distal portion of the colon, extending as far as the splenic flexure. Sparing of the rectum or involvement of the right side (proximal portion) of the colon alone is unusual in UC. The inflammatory process of UC is limited to the colon and does not involve, for example, the small intestine, stomach, or esophagus. In addition, UC is distinguished by a superficial inflammation of the mucosa that generally spares the deeper layers of the bowel wall. Crypt abscesses, in which degenerated intestinal crypts are filled with neutrophils, are also typical of UC (Rubin and Farber, supra).

In certain instances, with respect to UC, the variability of symptoms reflect differences in the extent of disease (i.e., the amount of the colon and rectum that are inflamed) and the intensity of inflammation. Disease starts at the rectum and moves "up" the colon to involve more of the organ. UC can be categorized by the amount of colon involved. Typically, patients with inflammation confined to the rectum and a short segment of the colon adjacent to the rectum have milder symptoms and a better prognosis than patients with more widespread inflammation of the colon.

In comparison with CD, which is a patchy disease with frequent sparing of the rectum, UC is characterized by a continuous inflammation of the colon that usually is more severe distally than proximally. The inflammation in UC is superficial in that it is usually limited to the mucosal layer and is characterized by an acute inflammatory infiltrate with neutrophils and crypt abscesses. In contrast, CD affects the entire thickness of the bowel wall with granulomas often, although not always, present. Disease that terminates at the ileocecal valve, or in the colon distal to it, is indicative of UC, while involvement of the terminal ileum, a cobblestone-like appearance, discrete ulcers, or fistulas suggests CD.

The different types of ulcerative colitis are classified according to the location and the extent of inflammation. As used herein in reference to UC, the term "clinical subtype" includes a classification of UC defined by a set of clinical criteria that distinguish one classification of UC from another. As non-limiting examples, subjects with UC can be classified as having ulcerative proctitis, proctosigmoiditis, left-sided colitis, pancolitis, fulminant colitis, and combinations thereof. Criteria relating to these subtypes have been described, for example, in Kornbluth et al., *Am. J. Gastroenterol.*, 99: 1371-85 (2004).

Ulcerative proctitis is a clinical subtype of UC defined by inflammation that is limited to the rectum. Proctosigmoiditis is a clinical subtype of UC which affects the rectum and the sigmoid colon. Left-sided colitis is a clinical subtype of UC which affects the entire left side of the colon, from the rectum to the place where the colon bends near the spleen and begins to run across the upper abdomen (the splenic flexure). Pancolitis is a clinical subtype of UC which affects the entire colon. Fulminant colitis is a rare, but severe form of pancolitis. Patients with fulminant colitis are extremely ill with dehydration, severe abdominal pain, protracted diarrhea with bleeding, and even shock.

In some embodiments, classification of the clinical subtype of UC is important in planning an effective course of treatment. While ulcerative proctitis, proctosigmoiditis, and left-sided colitis can be treated with local agents introduced through the anus, including steroid-based or other enemas and foams, pancolitis must be treated with oral medication so that active ingredients can reach all of the affected portions of the colon.

One skilled in the art understands that overlap can exist between clinical subtypes of UC and that a subject having UC can have more than one clinical subtype of UC. Similarly, the prognostic markers described herein can be associated with more than one clinical subtype of UC.

3. Patients with CD or UC

In some embodiments, the subjects of methods disclosed herein are patients with moderate to severe CD or a score of about 220 to 450 on the Crohn's Disease Activity Index (CDAI ranges from 0 to about 600, with higher scores indicating greater disease activity. In other embodiments, the subjects have moderate to severe UC or a Mayo Clinic score ranging from about 6 to 12 (Mayo Clinic scores range from 0 to 12 with higher scores indicating active disease), with a sigmoidoscopy subscore of at least 2, and disease that extends 15 cm or more from the anal verge.

In some embodiments, the subject has not received an anti-$\alpha 4 \beta 7$ integrin drug (e.g., vedolizumab). In some embodiments, the subject has not received an anti-TNF$\alpha$ therapy. The subject may be predicted to be nonresponsive to an anti-TNF$\alpha$ drug. In other embodiments, the subject has developed an intolerance to the anti-TNF$\alpha$ drug. In some instances, the subject has had an inadequate response to the anti-TNF$\alpha$ drug. In other instances, the subject has lost response to the anti-TNF$\alpha$ drug.

In some aspects of the present invention, the method is performed at baseline (e.g., prior to receiving an anti-$\alpha 4 \beta 7$ integrin drug). The presence or level of one or more predictive markers described herein may be detected or quantitated at a single time point. In other aspects, the method is performed during induction therapy (e.g., at week 0 to week 6 of anti-$\alpha 4 \beta 7$ integrin drug treatment). In some embodiments, the presence or level of one or more predictive markers are measured at one or more time points during induction therapy. In yet other aspects, the method is performed during maintenance therapy (e.g., at week 8 or later of anti-$\alpha 4 \beta 7$ integrin drug treatment). In some instances, the presence or level of one or more predictive markers are measured at one or more time points during maintenance therapy.

B. Markers for Predicting Response to Vedolizumab

A variety of IBD markers, including biochemical markers, serological markers, protein markers, genetic markers, and other clinical or echographic characteristics, are suitable for use in the methods of the present invention for predicting response to vedolizumab therapy. In certain aspects, prognostic methods described herein utilize the application of an algorithm (e.g., statistical analysis) to the presence or concentration level determined for one or more of the markers to aid or assist in a prognosis regarding whether a UC or CD patient will respond to vedolizumab therapy.

The following predictive markers are suitable for use in the present invention. The markers can make up a marker profile. Suitable markers include, but are not limited to, TNF$\alpha$, human serum albumin (HSA), VEGF, angiopoietin-1 (ANG-1), angiopoietin-2 (ANG-2), adenosine deaminase (ADA), serum $\alpha 4 \beta 7$ integrin, IL-12p40, C-reactive protein (CRP), MMP9, MAdCAM-1, VCAM-1, and ICAM-1.

In some embodiments, the methods provided herein include measuring/detecting the presence or level one or more, e.g., 1, 2, 3, 4, 5, 6, 7, 8, 9, 10, 11, 12, 13, 14, 15, 16, 17, 18, 19, 20 or more predictive markers. In some embodiments, the method includes detecting the presence or level of serum $\alpha 4 \beta 7$ integrin and MAdCAM-1. In some embodiments, the method includes detecting the presence or level of serum $\alpha 4 \beta 7$ integrin and TNF$\alpha$. In some embodiments, the method includes detecting the presence or level of serum $\alpha 4 \beta 7$ integrin and HSA. In some embodiments, the method includes detecting the presence or level of serum $\alpha 4 \beta 7$ integrin and ANG-1. In some embodiments, the method includes detecting the presence or level of serum $\alpha 4 \beta 7$ integrin and ANG-2. In some embodiments, the method includes detecting the presence or level of serum $\alpha 4 \beta 7$ integrin and IL-12p40. In some embodiments, the method includes detecting the presence or level of serum $\alpha 4 \beta 7$ integrin and CRP. In some embodiments, the method includes detecting the presence or level of serum $\alpha 4 \beta 7$ integrin and MMP9. In other embodiments, the method includes detecting the presence or level of serum $\alpha 4 \beta 7$ integrin and ICAM-1. In other embodiments, the method includes detecting the presence or level of serum $\alpha 4 \beta 7$ integrin and VCAM-1. In some aspects, the method includes detecting the presence or level of serum $\alpha 4 \beta 7$ integrin, MAdCAM-1, and one or more additional markers provided herein.

In some embodiments, the method includes detecting the presence or level of MAdCAM-1 and VCAM-1. In other embodiments, the method includes detecting the presence or level of MAdCAM-1 and ICAM-1. In some embodiments, the method includes detecting the presence or level of MAdCAM-1 and TNFα.

In some embodiments, the method includes detecting the presence or level of ANG-1, ADA, HSA, IL-12p40, MMP9, ICAM-1, VCAM-1, and serum α4β7 integrin. In some embodiments, the method includes detecting the presence or level of ANG-1, ADA, HSA, IL-12p40, MMP9, ICAM-1, and VCAM-1. In some embodiments, the method includes detecting the presence or level of ANG-1, ADA, HAS, IL-12p40, MMP9, ICAM-1, and VCAM-1.

In some embodiments, the methods include measuring/detecting the presence or level one or more, e.g., 1, 2, 3, 4, 5, 6, 7, 8, 9, 10, 11, 12, 13, 14, 15, 16, 17, 18, 19, 20 or more predictive markers at one or more, e.g., 1, 2, 3, 4, 5, 6, 7, 8, 9, 10 or more time points. In some embodiments, the method includes detecting the presence or level of one or more, e.g., 1, 2, 3, 4, 5, 6, 7, 8, 9, 10, 11, 12, 13, 14, 15, 16, 17, 18, 19, 20 or more predictive markers at, for example, baseline (prior to the administration of vedolizumab), post week 0 (immediately after the initial administration of the drug), week 2, week 4, week 6, week 8, week 10, week 12, week 14, week 16, week 18, week 20, week 22, week 24, week 26, week 28, week 30, week 32, week 34, week 36, week 38, week 40, week 42, week 44, week 46, week 48, week 50, or week 52 of drug treatment, or any combination thereof. In other instances, the presence or level of one or more predictive markers, e.g., 1, 2, 3, 4, 5, 6, 7, 8, 9, 10, 11, 12, 13, 14, 15, 16, 17, 18, 19, 20 or more predictive markers, is measured once a week or less often during the course of treatment.

In some embodiments, the presence or level of one or more, e.g., 1, 2, 3, 4, 5, 6, 7, 8, 9, 10, 11, 12, 13, 14, 15, 16, 17, 18, 19, 20 or more predictive markers are detected at baseline. In some embodiments, the presence or level of one or more, e.g., 1, 2, 3, 4, 5, 6, 7, 8, 9, 10, 11, 12, 13, 14, 15, 16, 17, 18, 19, 20 or more predictive markers are detected at week 2. In some embodiments, the presence or level of one or more, e.g., 1, 2, 3, 4, 5, 6, 7, 8, 9, 10, 11, 12, 13, 14, 15, 16, 17, 18, 19, 20 or more predictive markers are detected at week 4. In some embodiments, the presence or level of one or more, e.g., 1, 2, 3, 4, 5, 6, 7, 8, 9, 10, 11, 12, 13, 14, 15, 16, 17, 18, 19, 20 or more predictive markers are detected at week 6. In some embodiments, the presence or level of one or more, e.g., 1, 2, 3, 4, 5, 6, 7, 8, 9, 10, 11, 12, 13, 14, 15, 16, 17, 18, 19, 20 or more predictive markers are detected prior to the development of anti-drug antibodies. In other embodiments, the presence or level of one or more, e.g., 1, 2, 3, 4, 5, 6, 7, 8, 9, 10, 11, 12, 13, 14, 15, 16, 17, 18, 19, 20 or more predictive markers are detected prior to the development of anti-drug antibodies at any time point during maintenance therapy.

In certain instances, the presence or level of a particular biomarker is detected at the level of mRNA expression with an assay such as, for example, a hybridization assay or an amplification-based assay. In certain other instances, the presence or level of a particular biomarker is detected at the level of protein expression using, for example, an immunoassay (e.g., ELISA), an immunohistochemical assay or a proximity dual detection assay. Suitable ELISA kits for determining the presence or level of a biomarker in a sample such as a serum, plasma, saliva, or urine sample are available from, e.g., R&D Systems, Inc. (Minneapolis, Minn.), Neogen Corp. (Lexington, Ky.), Alpco Diagnostics (Salem, N.H.), Assay Designs, Inc. (Ann Arbor, Mich.), BD Biosciences Pharmingen (San Diego, Calif.), Invitrogen (Camarillo, Calif.), Calbiochem (San Diego, Calif.), CHEMICON International, Inc. (Temecula, Calif.), Antigenix America Inc. (Huntington Station, N.Y.), QIAGEN Inc. (Valencia, Calif.), Bio-Rad Laboratories, Inc. (Hercules, Calif.), and/or Bender MedSystems Inc. (Burlingame, Calif.). In some embodiments, the proximity dual detection assay is a CEER™ (Collaborative Enzyme Enhanced Reactive innumoassay) assay, an antibody-microarray based platform is utilized to form a unique "triple-antibody-enzyme-channeling" immuno-complex capable of measuring analytes of limited availability in a sample. A detailed description of CEER™ is found in, e.g., U.S. Pat. No. 8,163,499, which is hereby incorporated by reference in its entity for all purposes.

1. Growth Factors

The determination of the presence or level of one or more growth factors in a sample is also useful in the present invention. As used herein, the term "growth factor" includes any of a variety of peptides, polypeptides, or proteins that are capable of stimulating cellular proliferation and/or cellular differentiation. In certain aspects, the presence or level of at least one growth factor including, but not limited to, vascular endothelial growth factor (VEGF).

The term "VEGF" or "vascular endothelial growth factor" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 300, 400, 410, or more amino acids, to a human VEGF sequence shown below; (2) bind to antibodies, e.g., polyclonal antibodies, raised against an immunogen comprising an amino acid sequence shown below, or conservatively modified variants thereof; (3) bind to a VEGF binding protein; (4) compete with a naturally occurring VEGF ligand binding to a VEGF ligand binding protein; (5) induce vasculogenesis and/or angiogenesis in cells having a membrane-bound VEGF binding protein; (6) specifically hybridize under stringent hybridization conditions to a nucleic acid sequence shown below, or conservatively modified variants thereof; (7) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human VEGF mRNA sequence; and/or (8) have at least 25, often 50, 75, 100, 125 or 143 contiguous amino acid residues of a human VEGF polypeptide sequence.

The human VEGF polypeptide sequence is set forth in, e.g., Genbank Accession No. NP_001020537, NP_001020538, NP_001020539, NP_001020540, NP_001020541, NP_001028928, NP_001165093, NP_001165094, NP_001165095, NP_001165096, NP_001165097, NP_001165098, NP_001165099, NP_001165100, NP_001165101, NP_001191313, and NP_001191314. The human VEGF mRNA (coding) sequence is set forth in, e.g., Genbank Accession No. NM_001025366, NM_001025367, NM_001025368, NM_001025370, NM_001025356, NM_001033756, NM_001171622, NM_001171623, NM_00117624, NM_001171625, NM_001171626, NM_001171627, NM_001171628, NM_001171629, NM_001171630, NM_001204384, NM_001204385, and NM_003376. One skilled in the art will appreciate that VEGF is also known as vascular endothelial growth factor, VEGF1, VEGF-A, VEGFA, VPF, vascular permeability factor, and MVCD1.

One skilled in the art will appreciate that variants, isoforms, alternative sequences of VEGF are also useful in the present invention.

2. Intercellular Adhesion Molecule-1 (ICAM-1)

The term "ICAM-1" or "intercellular adhesion molecule 1" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 300, 400, 500, 525, or more amino acids, to a human ICAM-1 sequence shown below; (2) bind to antibodies, e.g., polyclonal antibodies, raised against an immunogen comprising an amino acid sequence shown below, or conservatively modified variants thereof; (3) bind to a ICAM-1 binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human ICAM-1 mRNA sequence; and/or (6) have at least 25, often 50, 75, 100, 125 or 143 contiguous amino acid residues of a human ICAM-1 polypeptide sequence. The human ICAM-1 polypeptide sequence is set forth in, e.g., Genbank Accession No. NP_000192. The human ICAM-1 mRNA (coding) sequence is set forth in, e.g., Genbank Accession No. NM_000201. One skilled in the art will appreciate that variants, isoforms, alternative sequences of ICAM-1 are also useful in the present invention.

ICAM-1 is a transmembrane cellular adhesion protein that is continuously present in low concentrations in the membranes of leukocytes and endothelial cells. Upon cytokine stimulation, the concentrations greatly increase. ICAM-1 can be induced by IL-1 and TNFα and is expressed by the vascular endothelium, macrophages, and lymphocytes. In IBD, proinflammatory cytokines cause inflammation by upregulating expression of adhesion molecules such as ICAM-1. The increased expression of adhesion molecules recruit more lymphocytes to the infected tissue, resulting in tissue inflammation (see, Goke et al., *J. Gastroenterol.,* 32:480 (1997); and Rijcken et al., *Gut,* 51:529 (2002)). ICAM-1 is encoded by the intercellular adhesion molecule 1 gene (ICAM1; Entrez GeneID: 3383; Genbank Accession No. NM_000201) and is produced after processing of the intercellular adhesion molecule 1 precursor polypeptide (Genbank Accession No. NP_000192).

3. Vascular Cell Adhesion Molecule-1 (VCAM-1)

The term "VCAM-1" or "vascular cell adhesion molecule 1" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 300, 400, 500, 600, 700, 720, 730, or more amino acids, to a human VCAM-1 sequence shown below; (2) bind to antibodies, e.g., polyclonal antibodies, raised against an immunogen comprising an amino acid sequence shown below, or conservatively modified variants thereof; (3) bind to a VCAM-1 binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human VCAM-1 mRNA sequence; and/or (6) have at least 25, often 50, 75, 100, 125 or 143 contiguous amino acid residues of a human VCAM-1 polypeptide sequence.

VCAM-1 is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to Tumor necrosis factor-alpha (TNFα) and Interleukin-1 (IL-1)). VCAM-1 is encoded by the vascular cell adhesion molecule 1 gene (VCAM1; Entrez GeneID: 7412) and is produced after differential splicing of the transcript (Genbank Accession No. NM_001078 (variant 1) or NM_080682 (variant 2)), and processing of the precursor polypeptide splice isoform (Genbank Accession No. NP_001069 (isoform a) or NP_542413 (isoform b)).

In certain instances, the presence or level of an IgSF CAM is detected at the level of mRNA expression with an assay such as, e.g., a hybridization assay or an amplification-based assay. In certain other instances, the presence or level of an IgSF CAM such as ICAM-1 or VCAM-1 is detected at the level of protein expression using, for example, an immunoassay (e.g., ELISA or an immuno electrochemiluminescence assay) or an immunohistochemical assay. Suitable antibodies and/or ELISA kits for determining the presence or level of ICAM-1 and/or VCAM-1 in a sample such as a tissue sample, biopsy, serum, plasma, saliva, urine, or stool are available from, e.g., Invitrogen (Camarillo, Calif.), Santa Cruz Biotechnology, Inc. (Santa Cruz, Calif.), and/or Abcam Inc. (Cambridge, Mass.).

4. Acute Phase Proteins

The determination of the presence or level of one or more acute-phase proteins in a sample is also useful in the present invention. Acute-phase proteins are a class of proteins whose plasma concentrations increase (positive acute-phase proteins) or decrease (negative acute-phase proteins) in response to inflammation. This response is called the acute-phase reaction (also called acute-phase response). Examples of positive acute-phase proteins include, but are not limited to, C-reactive protein (CRP).

The term "CRP" or "C-reactive protein" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 210, 220 or more amino acids, to a human CRP sequence shown below; (2) bind to antibodies, e.g., polyclonal antibodies, raised against an immunogen comprising an amino acid sequence shown below, or conservatively modified variants thereof; (3) bind to a CRP binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human CRP mRNA sequence; and/or (6) have at least 25, often 50, 75, 100, 125 or 143 contiguous amino acid residues of a human CRP polypeptide sequence.

CRP is a protein found in the blood in response to inflammation (an acute-phase protein). CRP is typically produced by the liver and by fat cells (adipocytes). It is a member of the pentraxin family of proteins. The human CRP polypeptide sequence is set forth in, e.g., Genbank Accession No. NP_000558. The human CRP mRNA (coding) sequence is set forth in, e.g., Genbank Accession No. NM_000567. One skilled in the art will appreciate that CRP is also known as PTX1, MGC88244, and MGC149895.

In certain instances, the presence or level of a particular acute-phase protein is detected at the level of mRNA expression with an assay such as, for example, a hybridization assay or an amplification-based assay. In certain other instances, the presence or level of a particular acute-phase protein is detected at the level of protein expression using, for example, an immunoassay (e.g., ELISA) or an immunohistochemical assay. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250; 6,406,862; and 7,439,019; and U.S. Patent Publication No. 2006/0019410. Additional methods for determining CRP levels include, e.g., immunoturbidimetry assays, rapid immunodiffusion assays, and visual agglutination assays. Suitable ELISA kits for determining the presence or level of SAA in a sample such as serum, plasma, saliva, urine, or stool are available from, e.g., Antigenix America Inc. (Huntington Station, N.Y.), Abazyme (Needham, Mass.), USCN Life (Missouri City, Tex.), and/or U.S. Biological (Swampscott, Mass.).

5. Mucosal Addressin Cell Adhesion Molecule (MAdCAM-1)

The term "mucosal addressin cell adhesion molecule" or "MAdCAM-1" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 281, 290 or more amino acids, to a human MAdCAM-1 sequence shown below; (2) bind to antibodies, e.g., polyclonal antibodies, raised against an immunogen comprising an amino acid sequence shown below, or conservatively modified variants thereof; (3) bind to a MAdCAM-1 binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human MAdCAM-1 mRNA sequence; and/or (6) have at least 25, often 50, 75, 100, 125 or 143 contiguous amino acid residues of a human MAdCAM-1 polypeptide sequence.

MAdCAM-1 is a predictive marker which is essential in mediating the infiltration of leucocytes into chronically inflamed tissues and plays a pivotal role in T-lymphocyte homing to the gut. The human MAdCAM-1 polypeptide sequence is set forth in, e.g., Genbank Accession No. NP_570118. The human MAdCAM-1 mRNA (coding) sequence is set forth in, e.g., Genbank Accession No. NM_130762. One skilled in the art will appreciate that variants, isoforms, alternative sequences of MAdCAM-1 are also useful in the present invention.

MAdCAM-1 is expressed by intestinal endothelium and its expression is increased under conditions of inflammation, including in the setting of inflammatory bowel disease (IBD). This molecule has been detected in body fluids, such as urine and serum, using a sandwich ELISA assay; however, the mechanism by which it is cleaved from the endothelial surface and released into circulation as soluble (s)-MAdCAM-1 is not well defined. s-MAdCAM-1 was detected during treatment with vedolizumab, a novel alpha-4 beta-7 ($\alpha 4\beta 7$) antagonist approved for treatment of ulcerative colitis (UC) and Crohn's disease (CD).

6. TNFα

The term "TNFα" or "tumor necrosis factor α" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 225, 230 or more amino acids, to a human TNFα sequence shown below; (2) bind to antibodies, e.g., polyclonal antibodies, raised against an immunogen comprising an amino acid sequence shown below, or conservatively modified variants thereof; (3) bind to a TNFα binding protein; (4) compete with a naturally occurring TNFα ligand binding to a TNFα ligand binding protein; (5) induce apoptosis in cells having a membrane-bound TNFα binding protein; (6) specifically hybridize under stringent hybridization conditions to a nucleic acid sequence shown below, or conservatively modified variants thereof; (7) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human TNFα mRNA sequence; and/or (8) have at least 25, often 50, 75, 100, 125 or 143 contiguous amino acid residues of a human TNFα polypeptide sequence. The human TNFα polypeptide sequence is set forth in, e.g., Genbank Accession No. NP_000585. The human TNFα mRNA (coding) sequence is set forth in, e.g., Genbank Accession No. NM_000594. One skilled in the art will appreciate that variants, isoforms, alternative sequences of TNFα are also useful in the present invention.

In other embodiments, an immunoassay such as a sandwich assay or ELISA can be used to measure TNFα. Non-limiting examples include Human TNFα High Sensitivity ELISA (Cat. No. BMS223HS, eBioscience, San Diego, Calif.), Erenna Human TNFα immunoassay (Cat. No. 03-0022-xx, Singulex, Alameda, Calif.), Human TNFα cytokine assay (Cat. No. K151BHA-5, Meso Scale Diagnostics (MSD), Rockville, Md.)) and a multi-marker immunoassay (e.g., as described in U.S. Pat. No. 8,450,069; Singulex).

7. Human Serum Albumin (HSA)

The term "human serum albumin" or "HSA" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 281, 300, 400, 500, 600, or more amino acids, to a human HSA sequence shown below; (2) bind to antibodies, e.g., polyclonal antibodies, raised against an immunogen comprising an amino acid sequence shown below, or conservatively modified variants thereof; (3) bind to an HSA binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human HSA mRNA sequence; and/or (6) have at least 25, often 50, 75, 100, 125 or 143 contiguous amino acid residues of a human HSA polypeptide sequence. The human HSA polypeptide sequence is set forth in, e.g., Genbank Accession No. NP_000468. The human HSA mRNA (coding) sequence is set forth in, e.g., Genbank Accession No. NM_000477. One skilled in the art will appreciate that variants, isoforms, alternative sequences of HSA are also useful in the present invention.

8. Angiopoietin-1 and -2 (ANG-1 and ANG-2)

The term "ANG-1" or "angiopoietin-1" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 281, 300, 400, 450, 475, or more amino acids, to a human ANG-1 sequence shown below; (2) bind to antibodies, e.g., polyclonal antibodies, raised against an immunogen comprising an amino acid sequence shown below, or conservatively modified variants thereof; (3) bind to a ANG-1 binding protein; (4) compete with a naturally occurring ANG-1 ligand binding to a ANG-1 ligand binding protein; (5) induce angiogenesis in cells having a membrane-bound ANG-1 binding protein; (6) specifically hybridize under stringent hybridization conditions to a nucleic acid sequence shown below, or conservatively modified variants thereof; (7) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human ANG-1 mRNA sequence; and/or (8) have at least 25, often 50, 75, 100, 125 or 143 contiguous amino acid residues of a human ANG-1 polypeptide sequence. The human ANG-1 polypeptide sequence is set forth in, e.g., Genbank Accession No. NP_001137 and NP_001146. The human ANG-1 mRNA (coding) sequence is set forth in, e.g., Genbank Accession No. NM_001146 and NM_001199859. One skilled in the art will appreciate that variants, isoforms, alternative sequences of ANG-1 are also useful in the present invention.

The term "ANG-2" or "angiopoietin-2" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, or 281 amino acids, to a human ANG-2 sequence shown below; (2) bind to antibodies, e.g., polyclonal antibodies, raised against an immunogen comprising an amino acid sequence shown below, or conservatively modified variants thereof; (3) bind to a ANG-2 binding protein; (4) compete with a naturally occurring ANG-2 ligand binding to a ANG-2 ligand binding protein; (5) induce angiogenesis in cells having a membrane-bound ANG-2 binding protein; (6) specifically hybridize under stringent hybridization conditions to a nucleic acid sequence shown below, or conservatively modified variants thereof; (7) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human ANG-2 mRNA sequence; and/or (8) have at least 25, often 50, 75, 100, 125 or 143 contiguous amino acid residues of a human ANG-2 polypeptide sequence. The human ANG-2 polypeptide sequence is set forth in, e.g., Genbank Accession Nos. NP_001112359, NP_001112360 and NP_001138. The human ANG-2 mRNA (coding) sequence is set forth in, e.g., Genbank Accession Nos. NM_001118887, NM_001118888 and NM_001147. One skilled in the art will appreciate that variants, isoforms, alternative sequences of ANG-2 are also useful in the present invention.

9. Adenosine Deaminase (ADA)

The term "adenosine deaminase" or "ADA" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, or 281 amino acids, to a human ADA sequence shown below; (2) bind to antibodies, e.g., polyclonal antibodies, raised against an immunogen comprising an amino acid sequence shown below, or conservatively modified variants thereof; (3) bind to an ADA binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400, 500, 600, 700, 800, 900, 1000, or more nucleotides, to a human ADA mRNA sequence; and/or (6) have at least 25, often 50, 75, 100, 125 or 143 contiguous amino acid residues of a human ADA polypeptide sequence. The human ADA polypeptide sequence is set forth in, e.g., Genbank Accession No. NP_000013. The human ADA mRNA (coding) sequence is set forth in, e.g., Genbank Accession No. NM_000022. One skilled in the art will appreciate that variants, isoforms, alternative sequences of ADA are also useful in the present invention.

10. α4β7 Integrin

The term "α4β7 integrin" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, or 281 amino acids, to a human α4β7 integrin sequence shown below; (2) bind to antibodies, e.g., polyclonal antibodies, raised against an immunogen comprising an amino acid sequence shown below, or conservatively modified variants thereof; (3) bind to an α4β7 integrin binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to a human α4β7 integrin mRNA sequence; and/or (6) have at least 25, often 50, 75, 100, 125 or 143 contiguous amino acid residues of a human α4β7 integrin polypeptide sequence. The human α4β7 integrin polypeptide sequence is set forth in, e.g., Genbank Accession Nos. NP_000876 and NP_000880. The human α4β7 integrin mRNA (coding) sequence is set forth in, e.g., Genbank Accession Nos. NM_000885 and NM_000889. One skilled in the art will appreciate that variants, isoforms, alternative sequences of α4β7 integrin are also useful in the present invention.

11. Hemoglobin (Hgb)

The term "hemoglobin" or "Hb" or "Hgb" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, or 281 amino acids, to a human Hb sequence shown below; (2) bind to antibodies, e.g., polyclonal antibodies, raised against an Hb immunogen comprising an amino acid sequence shown below, or conservatively modified variants thereof; (3) bind to an Hb binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to human Hb subunits alpha, beta, delta and/or gamma RNA sequences; and/or (6) have at least 25, often 50, 75, 100, 125 or 143 contiguous amino acid residues of human Hb subunits alpha, beta, delta and/or gamma polypeptide sequences.

The human hemoglobin alpha polypeptide sequence is set forth in, e.g., Genbank Accession No. NP_000558. The human hemoglobin alpha mRNA (coding) sequence is set forth in, e.g., Genbank Accession No. NM_000549. The human hemoglobin beta polypeptide sequence is set forth in, e.g., Genbank Accession No. NP_000509. The human hemoglobin beta mRNA (coding) sequence is set forth in, e.g., Genbank Accession No. NM_000518. The human hemoglobin delta polypeptide sequence is set forth in, e.g., Genbank Accession No. NP_000510. The human hemoglobin delta mRNA (coding) sequence is set forth in, e.g., Genbank Accession No. NM_000519. The human hemoglobin gamma polypeptide sequence is set forth in, e.g., Genbank Accession No. NP_000550 and NP_000175. The human hemoglobin gamma mRNA (coding) sequence is set forth in, e.g., Genbank Accession No. NM_000559 and NM_000184. One skilled in the art will appreciate that variants, isoforms, alternative sequences of the hemoglobin alpha, beta, delta and gamma subunits are also useful in the present invention.

12. Matrix Metalloproteinase 9 (MMP9)

The term "MMP9" or "matrix metalloproteinase 9" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 300, 400, 500, 600, 700, or 707 amino acids to a human MMP9 sequence shown below; (2) bind to antibodies, e.g., polyclonal antibodies, raised against an MMP9 immunogen comprising an amino acid sequence shown below, or conservatively modified variants thereof; (3) bind to an MMP9 binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400, 500, 1000, 1500, 2000, 2300, or more nucleotides, to a human MMP9 mRNA sequence; and/or (6) have at least 25, often 50, 75, 100, 125, 143 or more contiguous amino acid residues of a human MMP9 polypeptide sequences.

The human MMP9 polypeptide sequence is set forth in, e.g., Genbank Accession No. NP_004985. The human MMP9 mRNA (coding) sequence is set forth in, e.g., Genbank Accession No. NM_004994. One skilled in the art will appreciate that variants, isoforms, alternative sequences of MMP9 are also useful in the present invention.

13. IL-12p40

The term "IL-12p40" or "Il-12 subunit p40" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 300, or 328 amino acids to a human IL-12p40 sequence shown below; (2) bind to antibodies, e.g., polyclonal antibodies, raised against an IL-12p40 immunogen comprising an amino acid sequence shown below, or conservatively modified variants thereof; (3) bind to an IL-12p40 binding protein; (4) specifically hybridize under stringent hybridization conditions to a nucleic acid sequence shown below, or conservatively modified variants thereof; (5) have a nucleic acid sequence that has greater than about 90%, preferably greater than about 96%, 97%, 98%, 99%, or higher nucleotide sequence identity, preferably over a region of at least about 100, 200, 300, 400, 500, 600, 1000, 2000, 2300, or more nucleotides, to a human IL-12p40 mRNA sequence; and/or (6) have at least 25, often 50, 75, 100, 125 or 143 contiguous amino acid residues of a human IL-12p40 polypeptide sequence.

The human IL-12p40 polypeptide sequence is set forth in, e.g., Genbank Accession No. NP_002178. The human IL-12p40 mRNA (coding) sequence is set forth in, e.g., Genbank Accession No. NM_002187. One skilled in the art will appreciate that variants, isoforms, alternative sequences of IL-12p40 are also useful in the present invention.

14. Predicting Vedolizumab Response or Non-Response

In some embodiments, the presence of a higher level of TNFα in patient serum at baseline or at week 2 of vedolizumab treatment, compared to a cut-off value indicates that the patient is likely to have lower vedolizumab levels at week 6 compared to a cut-off value. In other embodiments, if a patient has a higher level of VEGF at baseline or at week 2 compared to a cut-off value, then the patient is likely to have a lower vedolizumab level at week 6 compared to a cut-off value. In yet other embodiments, if a patient has a higher level of ANG-2 at baseline or at week 2 compared to a cut-off value, then the patient is likely to have a lower vedolizumab level at week 6 compared to a cut-off value. In still other embodiments, if a patient has a higher level of CRP at baseline or at week 2 compared to a cut-off value, then the patient is likely to have a lower vedolizumab level at week 6 compared to a cut-off value. In some embodiments, if a patient has a higher level of VCAM-1 at baseline or at week 2 compared to a cut-off value, then the patient is likely to have a lower vedolizumab level at week 6 compared to a cut-off value. In some instances, the presence of a lower vedolizumab level at week 6 indicates that the patient has autoantibodies against vedolizumab. The cut-off value for a specific predictive marker can be established from a reference population of subjects who are likely to have higher vedolizumab levels at week 6. In some cases, the reference population includes subject who had a clinical response (e.g., a greater than or equal to 70-point decrease in CDAI score for CD; a reduction in the Mayo Clinical score of at least 3 points and a decrease of at least 30% from the baseline score, with a decrease of at least 1 point on the rectal bleeding score of 0 or 1 for UC) to vedolizumab. The lower level of vedolizumab may be relative or in comparison to the level of vedolizumab in a sample from a patient who has had a clinical response, is in clinical remission or does not have autoantibodies against vedolizumab. In some embodiments, the lower level of serum vedolizumab is less than about 33-34 µg/mL for a subject with CD or UC.

In some embodiments, the presence of a higher level of ANG-1 in patient serum at baseline compared to a cut-off value indicates that the patient is likely to have a higher vedolizumab level at week 6 compared to a cut-off value. In some embodiments, if a patient has higher ADA levels at baseline or at week 2 of vedolizumab treatment compared to a cut-off value, the patient has higher levels of vedolizumab compared to a cut-off value. In other embodiments, if the patient has a higher serum albumin level at week 2 compared to a cut-off value, the patient is likely to have a higher level of vedolizumab compared to a cut-off value. In another embodiment, if a patient has higher IL-12p40 levels at baseline or at week 2 of vedolizumab treatment compared to a cut-off value, the patient has higher levels of vedolizumab compared to a cut-off value. In yet other embodiments, if the patient has a higher MMP9 level at baseline or week 2 compared to a cut-off value, the patient is likely to have a higher level of vedolizumab compared to a cut-off value. In some embodiments, if the patient has a higher ICAM-1 level at baseline or week 2 compared to a cut-off value, the patient is likely to have a higher level of vedolizumab compared to a cut-off value. In one embodiment, if the patient has a higher serum α4β7 level at baseline or week 2 compared to a cut-off value, the patient is likely to have a higher level of vedolizumab compared to a cut-off value. In some instances, the presence of a higher vedolizumab level at week 6 indicates that the patient does not have autoantibodies against vedolizumab. In some cases, the cut-off value for a specific predictive marker is determined using a reference population of subjects. In some cases, the reference population includes subjects who have not had a clinical response (e.g., a greater than or equal to 70-point decrease in CDAI score; a reduction in the Mayo Clinical score of at least 3 points and a decrease of at least 30% from the baseline score, with a decrease of at least 1 point on the rectal bleeding score of 0 or 1 for UC) to vedolizumab. The higher level of vedolizumab may be relative to the level of vedolizumab in a sample from a patient who has autoantibodies against vedolizumab. In some embodiments, the higher level of serum vedolizumab is about 33-34 µg/mL or greater for a subject with CD or UC.

In some embodiments, if the patient has a lower Mad-CAM-1 level at baseline or week 2 compared to a cut-off value, the patient is likely to have a higher level of vedolizumab compared to a cut-off value. In other embodiments, if the patient has a lower TNFα level at baseline or week 2 compared to a cut-off value, the patient is likely to have a higher level of vedolizumab compared to a cut-off value. In some cases, the reference population includes subjects who have not had a clinical response (e.g., a greater than or equal to 70-point decrease in CDAI score for CD; a reduction in the Mayo Clinical score of at least 3 points and a decrease of at least 30% from the baseline score, with a decrease of at least 1 point on the rectal bleeding score of 0 or 1 for UC) to vedolizumab. The higher level of vedolizumab may be relative to the level of vedolizumab in a sample from a patient who has autoantibodies against vedolizumab. In some embodiments, the higher level of serum vedolizumab is about 33-34 µg/mL or greater for a subject with CD or UC.

In some embodiments, there is a positive association (correlation) between the level of vedolizumab at week 6 and the level of IL-12p40 at baseline. In some embodiments, there is a positive association (correlation) between the level of vedolizumab at week 6 and the level of MMP9 at week 2. In other embodiments, CRP levels at baseline are not associated with vedolizumab levels at week 6 of drug therapy.

In some embodiments for patients who are likely to have a clinical response to vedolizumab, for example, at week 6 of treatment, the level of serum α4β7 integrin increases and the level of MadCAM-1 decreases during the course of vedolizumab treatment. For instance, a CD or UC patient can undergo clinical response at week 6 after initiating a vedolizumab induction treatment regimen if the level of serum α4β7 integrin increases and the level of MadCAM-1 decreases compared to baseline.

In some embodiments for patients (e.g., CD or UC patients) who are likely to undergo clinical remission, for example, at week 6 or week 52 of treatment, the level of serum α4β7 integrin increases and the level of MadCAM-1 decreases during therapy such as from a first time point to a later time point. In some cases, a CD or UC patient can undergo clinical remission upon receiving a vedolizumab maintenance treatment regimen if the patient has an increase in serum α4β7 integrin levels and a decrease in MadCAM-1 levels relative to baseline levels.

In some embodiments, if a patient has a high TNFα, VEGF, ANG-2, CRP, and/or VCAM-1 level(s) at baseline, the patient is likely to develop autoantibodies against vedolizumab. Those with a high TNFα level during induction therapy are predicted to develop autoantibodies. For instance, a patient with a high baseline level of TNFα is likely to have autoantibodies against vedolizumab at week 2 and week 6.

Patients with low level(s) of MadCAM-1, VCAM-1, and/or TNFα are not predicted to develop such autoantibodies. In other embodiments, patients with a high level(s) of ANG-1, ADA, HSA, IL-12p40, MMP9, ICAM-1 and/or serum α4β7 integrin at baseline are not likely to develop autoantibodies to an anti-α4β7 integrin drug. For instance, patients with a higher HSA level are predicted to not develop autoantibodies against vedolizumab at week 6 or week 14.

A patient with autoantibodies against an anti-α4β7 integrin drug may have had higher levels of TNFα, VEGF, ANG-2, CRP, VCAM-1 or any combination thereof at baseline or week 2 of therapy, compared to a patient who does not have the autoantibodies. A patient who does not have the autoantibodies may have had a lower level of MadCAM-1, VCAM-1, and TNFα, and higher levels ANG-1, ADA, HSA, IL-12p40, MMP9, ICAM-1, serum α4β7 integrin, or any combination thereof at baseline or week 2, compared to a patient with the autoantibodies.

Provided herein are methods for treating a subject with CD or UC with an anti-α4β7 integrin drug such as vedolizumab. The method includes administering the drug to a subject having CD or UC and having a level of ANG-1, ADA, HSA, IL-12p40, MMP9, ICAM-1 and/or serum α4β7 integrin that is higher than a corresponding reference value. Alternatively, the method may include administering the drug to a subject having CD or UC and having a level of MadCAM-1, VCAM-1 or TNFα that is lower than a corresponding reference value. In some cases, the UC subject administered vedolizumab may undergo mucosal healing. In other cases, the CD or UC subject receiving the drug may be withdrawn from steroid treatment or undergo glucocorticoid-free remission (e.g., clinical remission without glucocorticoid therapy).

C. Setting Cut-Off Values

Once the sample(s) from the human subject have been assayed for the criteria listed above, a value is generated for predicting likelihood of clinical response (e.g., as defined by the Physician's Global Assessment for CD or UC, the Crohn's Disease Activity Index, the Mayo Clinic Score, or any other standard assessment criteria or scale for IBS) to vedolizumab or likelihood of having clinical remission (e.g., as defined by the Physician's Global Assessment for CD or UC, the Crohn's Disease Activity Index, the Mayo Clinic Score, or any other standard assessment criteria or scale for IBS). When two or more predictive markers or other criteria are used in the method described herein, the level of each marker can be weighted and combined. Thus, a test value may be provided by (a) weighting the determined level of each marker with a predefined coefficient, and (b) combining the weighted level to provide a test value. The combining step can be either by straight addition or averaging (i.e., weighted equally) or by a different predefined coefficient.

Once generated, the value from a sample can be compared to one or more cut-off or threshold value(s) to provide a likelihood of clinical response or clinical remission. In order to establish a cut-off value for practicing the method, a reference population of subjects can be used. In some embodiments, a population of patients with CD or UC can be used. In some instances, the patients have had a clinical response to vedolizumab. In other instances, the patients have not had a clinical response to vedolizumab or have autoantibodies against vedolizumab. Alternatively, the patients may have a clinical response to the anti-α4β7 integrin drug. In some embodiments, the patients are in clinical remission from CD or in clinical remission from UC.

In some embodiments, these patients are within the appropriate parameters, if applicable, for the purpose of screening for and/or monitoring CD or UC using the methods of the present disclosure. Optionally, the patients are of similar age or similar ethnic background. The status of the selected patients can be confirmed by well established, routinely employed methods including but not limited to general physical examination of the individuals and general review of their medical history. Furthermore, the selected group of patients will generally be of sufficient size, such that the average value in the sample obtained from the group can be reasonably regarded as representative of a particular indication, for example indicative of reoccurrence of CD or UC or not after a set period of time (e.g., 2 years) after treatment.

Once an average value is established based on the individual values found in each subject of the selected group, this average or median or representative value or profile can be used as a cut-off value. For example, a sample value over the cut-off value can indicate a more than average likelihood of clinical response or clinical remission depending on the predictive marker used. In some embodiments, a standard deviation is also determined during the same process. In some cases, separate cut-off values may be established for separately defined groups having distinct characteristics such as age, gender, or ethnic background.

According to the methods described herein, the sample is compared to one or more reference or threshold values. In some embodiments, the sample value is deemed "high" if it is at least 1, 2, 3, 4, 5, 10, 15, 20 or more standard deviations greater than the reference value subjects. In other embodiments, the sample value is below the threshold if the sample value is at least 1, 2, 3, 4, 5, 10, 15, 20 or more standard deviations lower than the reference or threshold value.

In some embodiments, a computer-based analysis program is used to translate the raw data generated by the detection methods described herein (e.g., the presence, absence, or amount of a given marker or markers) into a score of predictive value to a clinician.

The predictive marker profile or score, as determined according to the methods above, can predict that the patient has an above-average likelihood of clinical response or remission. In some cases, the patient has a high likelihood of clinical response or remission. The score can also predict that the patient has an average or below-average likelihood oft clinical response or remission. In such instances, the patient can have a low or intermediate likelihood of clinical response or remission.

D. Markers for Measuring Anti-α4β7 Integrin Drug and Anti-Drug Antibody (ADA) Levels In some embodiments, the method comprises determining the presence and/or level of anti-α4β7 integrin drug (e.g., level of free anti-α4β7 integrin therapeutic antibody such as vedolizumab) and/or anti-drug antibody (ADA) (e.g., level of autoantibody to the anti-α4β7 integrin drug such as HAHA) in a patient sample (e.g., a serum sample from a patient on anti-α4β7 integrin drug therapy) at multiple time points, e.g., before, during, and/or after the course of therapy.

In some embodiments, the presence and/or level of anti-α4β7 integrin drug and/or ADA is determined with a homogeneous mobility shift assay (HMSA) using size exclusion chromatography. These methods are described in U.S. Pat. Nos. 8,574,855, and 8,865,417 and U.S. Patent Publication Nos. 2014/0051184 and 2014/0141983, the disclosures of which are hereby incorporated by reference in their entirety for all purposes. The methods are particularly useful for measuring the presence or level of α4β7 integrin inhibitors as well as autoantibodies (e.g., HACA, HAHA, etc.) that are generated against them.

In other embodiments, the presence and/or level of anti-α4β7 integrin drug and/or ATV is determined with an immunoassay, such as an enzyme-linked immunosorbent assay (ELISA). In yet other embodiments, the presence and/or level of anti-α4β7 integrin drug and/or ATV is determined with a flow cytometry assay such as FACS.

E. Statistical Analysis

In some aspects, the present invention provides methods for selecting anti-α4β7 integrin drug therapy, optimizing anti-α4β7 integrin drug therapy, reducing toxicity associated with anti-α4β7 integrin drug therapy, and/or monitoring the efficacy of anti-α4β7 integrin drug treatment by applying one or more statistical algorithm to one or more (e.g., a combination of two, three, four, five, six, seven, eight, nine, ten, eleven, twelve or more) pharmacodynamic and/or predictive markers. In particular embodiments, quantile analysis is applied to the presence and/or level of one or more markers to guide treatment decisions for patients receiving anti-α4β7 integrin drug therapy. In other embodiments, one or a combination of two of more learning statistical classifier systems are applied to the presence and/or level of one or more markers to guide treatment decisions for patients receiving anti-α4β7 integrin drug therapy. The statistical analyses of the methods of the present invention advantageously assist in determining when or how to adjust or modify (e.g., increase or decrease) the subsequent dose of an anti-α4β7 integrin drug, to combine an anti-α4β7 integrin drug (e.g., at an increased, decreased, or same dose) with one or more immunosuppressive agents such as methotrexate (MTX) or azathioprine (AZA), and/or to change the current course of therapy (e.g., switch to a different anti-α4β7 integrin drug).

The term "statistical analysis" or "statistical algorithm" or "statistical process" includes any of a variety of statistical methods and models used to determine relationships between variables. In the present invention, the variables are the presence or level of at least one marker of interest. Any number of markers can be analyzed using a statistical analysis described herein. For example, the presence or level of 1, 2, 3, 4, 5, 6, 7, 8, 9, 10, 11, 12, 13, 14, 15, 16, 17, 18, 19, 20, 25, 30, 35, 40, 45, 50, 55, 60, or more markers can be included in a statistical analysis. In one embodiment, logistic regression is used. In another embodiment, linear regression is used. In yet another embodiment, ordinary least squares regression or unconditional logistic regression is used. In certain preferred embodiments, the statistical analyses of the present invention comprise a quantile measurement of one or more markers, e.g., within a given population, as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In certain embodiments, the present invention involves detecting or determining the presence and/or level (e.g., magnitude) of one or more markers of interest using quartile analysis. In this type of statistical analysis, the level of a marker of interest is defined as being in the first quartile (<25%), second quartile (25-50%), third quartile (51%-<75%), or fourth quartile (75-100%) in relation to a reference database of samples. These quartiles may be assigned a quartile score of 1, 2, 3, and 4, respectively. In certain instances, a marker that is not detected in a sample is assigned a quartile score of 0 or 1, while a marker that is detected (e.g., present) in a sample (e.g., sample is positive for the marker) is assigned a quartile score of 4. In some embodiments, quartile 1 represents samples with the lowest marker levels, while quartile 4 represent samples with the highest marker levels. The reference database of samples can include a large spectrum of patients with a TNFα-mediated disease or disorder such as, e.g., IBD. From such a database, quartile cut-offs can be established. A non-limiting example of quartile analysis suitable for use in the present invention is described in, e.g., Mow et al., *Gastroenterology*, 126:414-24 (2004).

In some embodiments, the statistical analyses of the present invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a decision/classification tree (e.g., random forest (RF) or classification and regression tree (C&RT)) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, the Cox Proportional-Hazards Model (CPHM), perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the $SVM^{light}$ software developed by Thorsten Joachims (Cornell University) or using the LIBSVM software developed by Chih-Chung Chang and Chih-Jen Lin (National Taiwan University).

The various statistical methods and models described herein can be trained and tested using a cohort of samples (e.g., serological and/or genomic samples) from healthy individuals and patients with a TNFα-mediated disease or disorder such as, e.g., IBD (e.g., CD and/or UC) or rheumatoid arthritis. For example, samples from patients diagnosed by a physician, preferably by a gastroenterologist, as having IBD or a clinical subtype thereof using a biopsy, colonoscopy, or an immunoassay as described in, e.g., U.S. Pat. No. 6,218,129, are suitable for use in training and testing the statistical methods and models of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from healthy individuals can include those that were not identified as IBD samples. One skilled in the art will know of additional techniques and diagnostic criteria for obtaining a cohort of patient samples that can be used in training and testing the statistical methods and models of the present invention.

F. Predictive Modeling

In certain aspects, the present invention provides pharmacokinetic models to predict the likelihood of developing anti-drug antibodies.

Pharmacokinetic models are ways to mathematically understand the fate of drugs in vivo. In a one compartment model, the drug-concentration time profile shows a monophasic response, and is described by a single exponential. In addition, the body is assumed to be a homogeneous unit with instantaneous distribution of the drug. A one-compartment model shows a linear relationship between log concentrations in plasma ($C_p$) versus time.

A two-compartment model resolves the body into two units, a central unit and a peripheral unit. In the two-compartment model, the log concentration in plasma ($C_p$) versus time profile is biphasic. In the biphasic model, there is a rapid decline in drug concentration followed by a slower decline. D. Ternant et al., Ther Drug Monit, 30(4), 523-529 (2008), showed that infliximab pharmacokinetics followed a two compartment model, with an elimination half-life of close to 3 weeks.

In other aspects, the present invention provides an algorithmic model to predict patient response to anti-α4β7 integrin drug. The model uses one or more markers such as an inflammatory marker which include cytokines and chemokines and the like, a signaling molecule, an acute phase protein, a cellular adhesion molecule and a combination thereof. The markers also include the presence or absence of ADA, the levels of α4β7 integrin, the levels of MAdCAM-1, the concentration or levels of anti-α4β7 integrin drugs and the like.

An algorithmic model includes any of a variety of statistical methods and models used to determine relationships between variables. In the present invention, the variables are the presence or level of at least one marker of interest. Any number of markers can be analyzed using a statistical analysis described herein (see, "Statistical Analysis" section). For example, the presence or level of 1, 2, 3, 4, 5, 6, 7, 8, 9, 10, 11, 12, 13, 14, 15, 16, 17, 18, 19, 20, 25, or more markers can be included in a statistical analysis.

In particular embodiments, quantile analysis is applied to the presence and/or level of one or more markers to guide treatment decisions for patients receiving anti-α4β7 integrin drug therapy. In other embodiments, one or a combination of two of more learning statistical classifier systems are applied to the presence and/or level of one or more markers to guide treatment decisions for patients receiving anti-α4β7 integrin drug therapy. The statistical analyses of the methods of the present invention advantageously assist in determining when or how to adjust or modify (e.g., increase or decrease) the subsequent dose of an anti-α4β7 integrin drug, to combine an anti-α4β7 integrin drug (e.g., at an increased, decreased, or same dose) with one or more immunosuppressive agents such as methotrexate (MTX) or azathioprine (AZA), and/or to change the current course of therapy (e.g., switch to a different anti-α4β7 integrin drug).

The algorithmic model includes the level or concentration of the one or more markers along with a statistic algorithm such as a learning statistical algorithm. In certain instances, the model has been trained with known outcomes using a training set cohort of samples. The algorithm is then validated using a validation cohort. Patient unknown samples can then be predicted based on the trained algorithms.

In some aspects, the present invention provides a system for predicting the level of an anti-α4β7 integrin drug in a subject at a later time point during a course of therapy with the anti-α4β7 integrin drug. In other aspects, the present invention provides a system for predicting whether a subject will develop autoantibodies to an anti-α4β7 integrin drug at a later time point during a course of therapy with the anti-α4β7 integrin drug. In yet other aspects, the present invention provides a system for predicting a clinical outcome of a subject at a later time point during a course of therapy with the anti-α4β7 integrin drug.

In certain embodiments, the system comprises: a data acquisition module configured to produce a data set comprising one or more predictor variables for the subject determined at an earlier time point during the course of therapy and/or prior to the initiation of the course of therapy; a data processing module configured to process the data set by applying a statistical analysis to the data set to produce a statistically derived decision predicting the level of the anti-α4β7 integrin drug or predicting whether the subject will develop autoantibodies to the anti-α4β7 integrin drug or predicting a clinical outcome of the subject receiving the anti-α4β7 integrin drug based upon the one or more predictor variables; and a display module configured to display the statistically derived decision.

In some embodiments, the system includes an intelligence module, such as a computer, having a processor and memory module. The intelligence module may also include communication modules for transmitting and receiving information over one or more direct connections (e.g., USB, Firewire, or other interface) and one or more network connections (e.g., including a modem or other network interface device). The memory module may include internal memory devices and one or more external memory devices. The intelligence module also includes a display module, such as a monitor, screen, or printer. In one aspect, the intelligence module receives data such as patient test results from a data acquisition module such as a test system, either through a direct connection or over a network. For example, the test system may be configured to run multianalyte tests on one or more patient samples and automatically provide the test results to the intelligence module. The data may also be provided to the intelligence module via direct input by a user or it may be downloaded from a portable medium such as a compact disk (CD) or a digital versatile disk (DVD). The test system may be integrated with the intelligence module, directly coupled to the intelligence module, or it may be remotely coupled with the intelligence module over the network. The intelligence module may also communicate data to and from one or more client systems over the network as is well known. For example, a requesting physician or healthcare provider may obtain and view a report from the intelligence module, which may be resident in a laboratory or hospital, using a client system.

The network can be a LAN (local area network), WAN (wide area network), wireless network, point-to-point network, star network, token ring network, hub network, or other configuration. As the most common type of network in current use is a TCP/IP (Transfer Control Protocol and Internet Protocol) network such as the global internetwork of networks often referred to as the "Internet" with a capital "I," that will be used in many of the examples herein, but it should be understood that the networks that the present invention might use are not so limited, although TCP/IP is the currently preferred protocol.

Several elements in the system may include conventional, well-known elements that need not be explained in detail here. For example, the intelligence module could be implemented as a desktop personal computer, workstation, mainframe, laptop, etc. Each client system could include a desktop personal computer, workstation, laptop, cell phone, tablet, PDA, or any WAP-enabled device or any other computing device capable of interfacing directly or indirectly to the Internet or other network connection. A client system typically runs an HTTP client, e.g., a browsing program, such as Microsoft's Internet Explorer™ browser, Google's Chrome™ browser, or a WAP-enabled browser or mobile application in the case of a cell phone, tablet, PDA, or other wireless device, or the like, allowing a user of the client system to access, process, and view information and pages available to it from the intelligence module over the network. Each client system also typically includes one or more user interface devices, such as a keyboard, a mouse, touch screen, pen, or the like, for interacting with a graphical user interface (GUI) provided by the browser on a display (e.g., monitor screen, cell phone or tablet screen, LCD display, etc.) in conjunction with pages, forms, and other information provided by the intelligence module. As discussed above, the present invention is suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN, or the like.

According to one embodiment, each client system and all of its components are operator configurable using applications, such as a browser, including computer code run using a central processing unit such as an Intel® Pentium® processor or the like. Similarly, the intelligence module and all of its components might be operator configurable using application(s) including computer code run using a central processing unit such as an Intel® Pentium® processor or the like, or multiple processor units. Computer code for operating and configuring the intelligence module to process data and test results as described herein is preferably downloaded and stored on a hard disk, but the entire program code, or portions thereof, may also be stored in any other volatile or non-volatile memory medium or device as is well known, such as a ROM or RAM, or provided on any other computer readable medium capable of storing program code, such as a compact disk (CD) medium, digital versatile disk (DVD) medium, a floppy disk, ROM, RAM, and the like.

The computer code for implementing various aspects and embodiments of the present invention can be implemented in any programming language that can be executed on a computer system such as, for example, in C, C++, C#, HTML, Java, JavaScript, or any other scripting language, such as VBScript. Additionally, the entire program code, or portions thereof, may be embodied as a carrier signal, which may be transmitted and downloaded from a software source (e.g., server) over the Internet, or over any other conventional network connection as is well known (e.g., extranet, VPN, LAN, etc.) using any communication medium and protocols (e.g., TCP/IP, HTTP, HTTPS, Ethernet, etc.) as are well known.

III. Examples

The present invention will be described in greater detail by way of specific examples. The following examples are offered for illustrative purposes, and are not intended to limit the present invention in any manner. Those of skill in the art will readily recognize a variety of noncritical parameters which can be changed or modified to yield essentially the same results.

Example 1

Methods for Predicting Response to Vedolizumab Based on the Presence or Level of One or More Biomarkers in a Patient Sample The aim of this example was to determine whether one or more markers can predict a response to therapy in IBD patients treated with vedolizumab. The markers tested included vedolizumab, antibodies against vedolizumab, TNFα, human serum albumin (HSA), VEGF, angiopoietin-1 (ANG-1), angiopoietin-2 (ANG-2), adenosine deaminase (ADA), serum α4β7 integrin (α4β7), matrix metalloproteinase 9 (MMP9), MAdCAM-1, hemoglobin (Hb), C-reactive protein (CRP), VCAM-1, and ICAM-1.

Sera were obtained from patients with IBD prior to the onset of vedolizumab therapy with (5 patients with ulcerative colitis and 7 patients with Crohn's disease) and after initiation of vedolizumab therapy (week 2 and 6). Concentrations of s-MAdCAM-1, TNFα, serum α4β7 integrin, vedolizumab, and antibodies to vedolizumab were measured by Collaborative Enzyme Enhanced Reactive assay (CEER™), an ultrasensitive enzyme linked immunoassay, and by homogenous mobility shift assay (HMSA). See, e.g., Wang et al., J Immunol Methods, 382:177-188 (2012), Kim et al., Proteome Sci; 9:75, 2011; Tao et al., Sci Signal, 7:rs29, 2014; and Elkabets et al., Sci Transl Med, 5:196ra99 (2013). In addition, the markers human serum albumin (HSA), VEGF, angiopoietin-1 (ANG-1), antiopoietin-2 (ANG-2), adenosine deaminase (ADA), MMP9, hemoglobin (Hb), C-reactive protein (CRP), VCAM-1, ICAM-1, TWEAK, and IL-20p40 were also measured by ELISA or CEER™.

Results: The mean age of patients with IBD was 42.8 years old with a mean baseline albumin of 3.9 g/dL, hemoglobin of 12.2 g/dL, and CRP of 67 mg/L. The mean concentration of s-MAdCAM-1 was 25,843 pg/mL in patients with IBD prior to initiation of vedolizumab and decreased to 3288 pg/mL at week 6 after two induction doses of vedolizumab. Soluble α4β7 concentration increased from a mean of 1360 pg/mL at baseline to 3880 pg/mL at week 6. Mean vedolizumab concentrations were 38.3 µg/mL at week 2 and 29.0 µg/mL at week 6. There was no significant change in concentrations of CRP or TNFα during induction therapy with vedolizumab. Higher baseline albumin concentrations correlated with higher vedolizumab concentrations at week 6 (adjusted R-squared=0.34); however, TNFα concentrations at baseline correlated with lower vedolizumab concentrations at week 6 (Adjusted R-square=0.87). The correlation between specific marker pairs at baseline and at week 2 are provided in Table 1.

TABLE 1

Subject Characteristics

|  | N | Mean | Q1 | Median | Q3 |
|---|---|---|---|---|---|
| age | 12 | 42.833333333333 | 34.5 | 40 | 56.75 |
| baseline alb | 12 | 3.875 | 3.275 | 4 | 4.375 |
| baseline hgb | 12 | 12.233333333333 | 11.225 | 11.7 | 13.175 |
| CRP ng/mL_baseline | 9 | 6684.2222222222 | 1682 | 4024 | 12117 |
| SAA ng/mL_baseline | 9 | 39822 | 2307.5 | 13891 | 80165.5 |
| sICAM-1 ng/mL_baseline | 9 | 394.11111111111 | 265 | 301 | 443 |
| sVCAM-1 ng/mL_baseline | 9 | 733.88888888889 | 475 | 576 | 941 |
| a4b7 pg/ml_baseline | 9 | 1360.1111111111 | 176.5 | 346 | 999 |
| Madcam pg/ml_baseline | 9 | 25843.333333333 | 17765.5 | 19783 | 36125 |
| ADA pg/ml_baseline | 9 | 1937.8888888889 | 784.5 | 1625 | 2257 |
| TNFa pg/ml_baseline | 9 | 8.3555555555556 | 3.95 | 6.1 | 13.25 |
| Ang1_baseline | 9 | 44265.555555556 | 34005 | 43250 | 53440 |
| MMP9_baseline | 9 | 1487488.8888889 | 829250 | 1311000 | 1972500 |
| P40_baseline | 9 | 1020.7055555556 | 328.375 | 437.6 | 1837.75 |
| Tweak_baseline | 9 | 304.9 | 213.2 | 328 | 404.75 |
| Ang2_baseline | 9 | 7234.6444444444 | 902.3 | 1671 | 6907 |
| VEGF pg/mL | 9 | 294.78244444 | 96.57 | 147.284 | 509.87 |
| Vedo ug/ml_wk6 | 7 | 28.971428571429 | 11.31 | 26.33 | 51.92 |
| CRP ng/mL_wk6 | 7 | 5960.5714285714 | 482 | 4213 | 11962 |
| SAA ng/mL_wk6 | 7 | 19099.714285714 | 1635 | 12908 | 42020 |
| sICAM-1 ng/mL_wk6 | 7 | 350.14285714286 | 270 | 291 | 507 |
| sVCAM-1 ng/mL_wk6 | 7 | 592.85714285714 | 460 | 520 | 855 |
| a4b7 pg/ml_wk6 | 7 | 3880.4285714286 | 2696 | 3782 | 4195 |
| Madcam pg/ml_wk6 | 7 | 3288 | 2409 | 2890 | 3249 |
| ADA pg/ml_wk6 | 7 | 1109.7142857143 | 801 | 905 | 1174 |
| TNFa pg/ml_wk6 | 7 | 4.6142857142857 | 2.1 | 4.3 | 6.6 |
| Ang1_wk6 | 7 | 38805.714285714 | 30520 | 37580 | 52100 |
| MMP9_wk6 | 7 | 879657.14285714 | 589600 | 924400 | 1159000 |
| P40_wk6 | 7 | 342.30714285714 | 188.3 | 215.35 | 480.3 |
| Tweak_wk6 | 7 | 288.12857142857 | 175.7 | 342.2 | 374.3 |
| Ang2_wk6 | 7 | 3110.8571428571 | 638.7 | 3184 | 6416 |

Figure 1B:
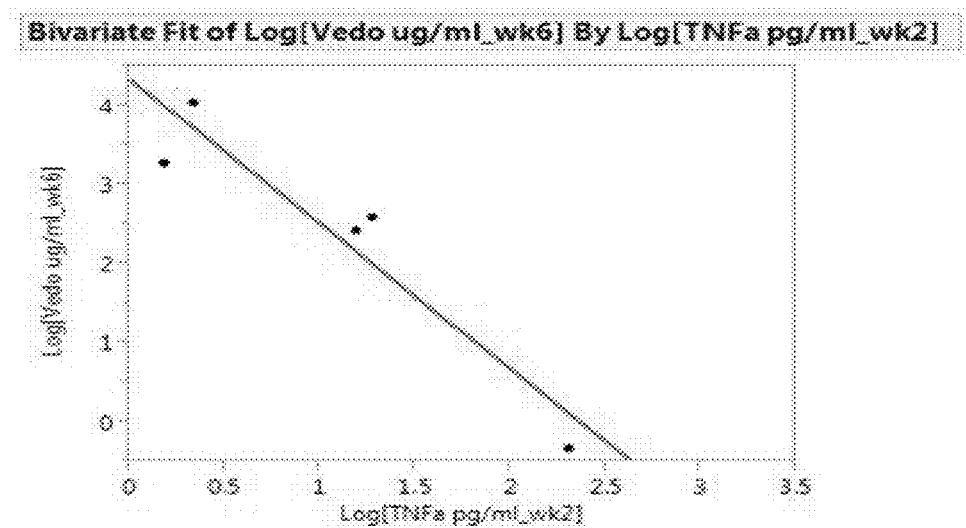
Figure 2:
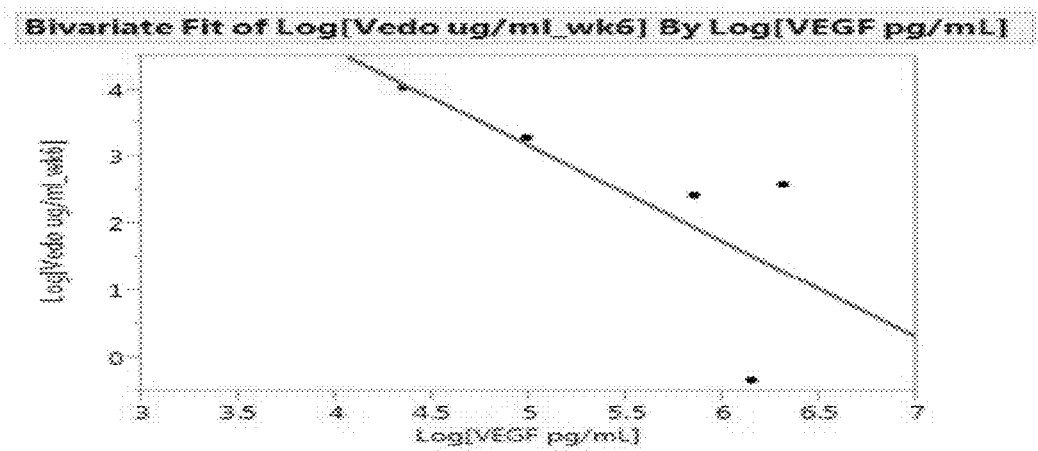
FIG. 2 shows a diagram of an exemplary embodiment of the present invention that shows higher VEGF levels at baseline result in lower vedolizumab at week 6.
Figure 3A:
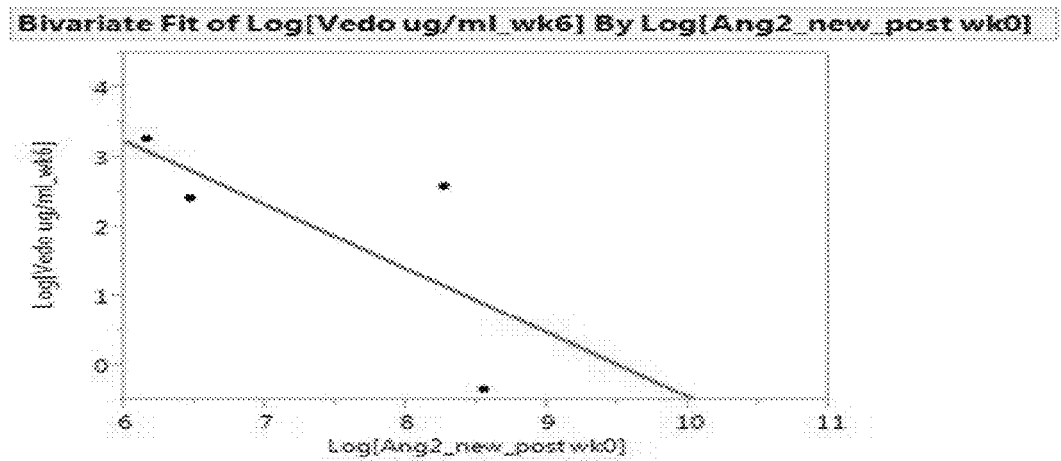
FIGS. 3A and 3B show the association between two angiogenesis markers ANG-1 and ANG-2 and vedolizumab levels.
Figure 3B:
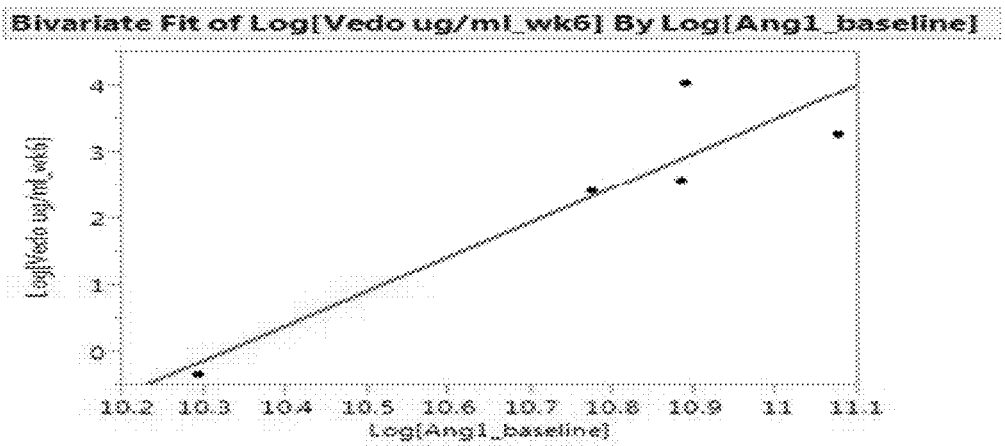
Figure 4A:
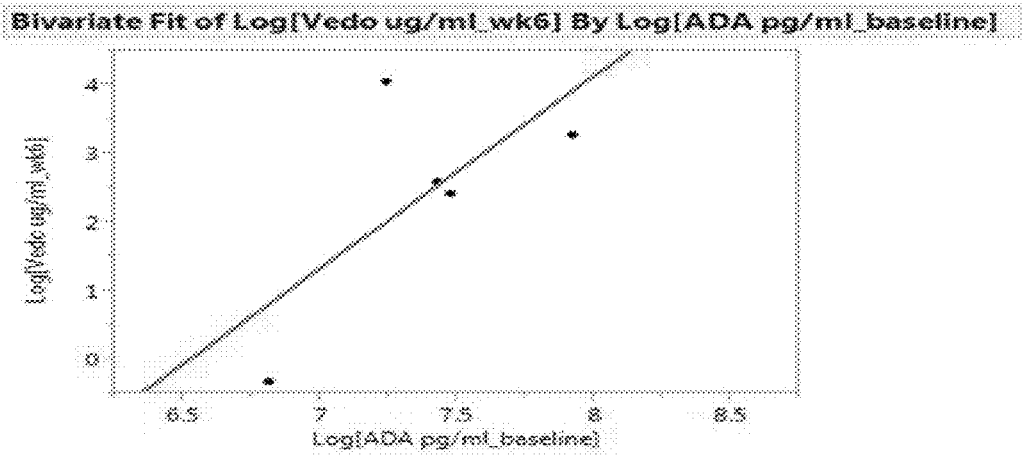
FIGS. 4A and 4B show the relationship between level of adenosine deaminase (ADA) and vedolizumab during therapy.
Figure 4B:
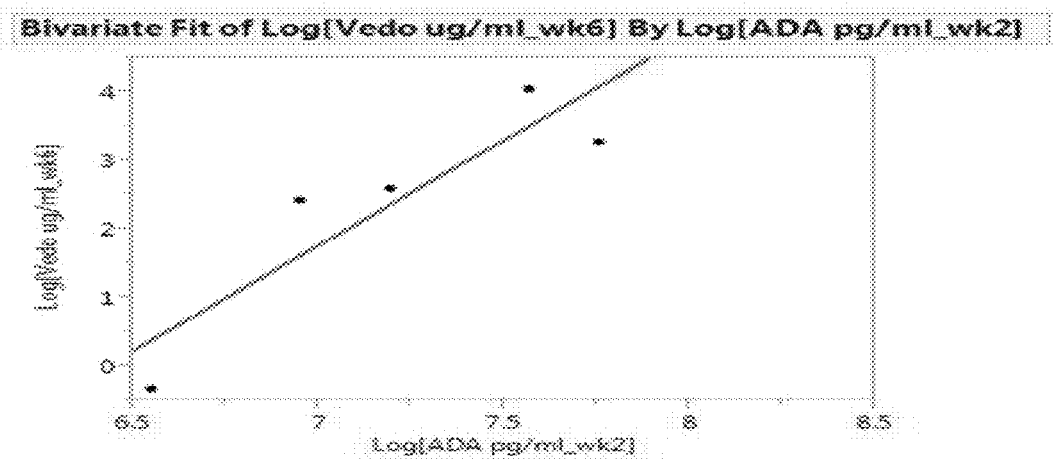
Figure 5A:
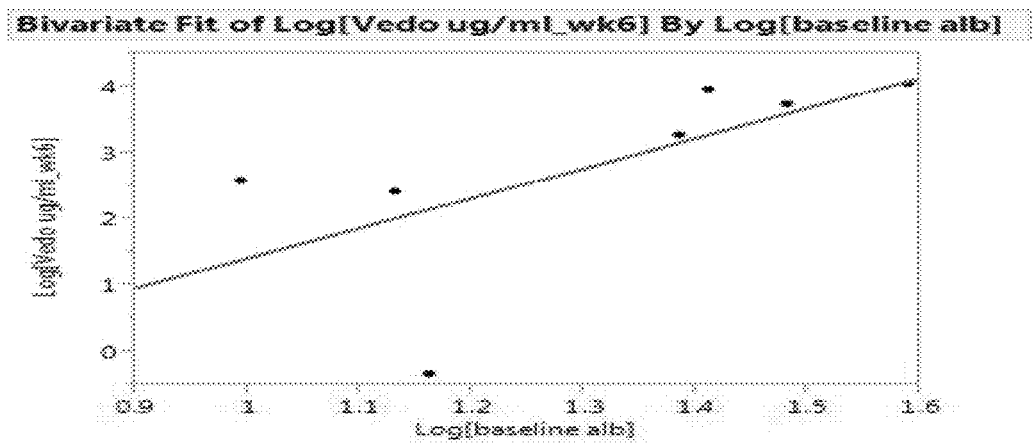
FIGS. 5A and 5B provide bivariate fit log graphs used to determine whether a specific biomarker is associated with the level of vedolizumab.
Figure 5B:
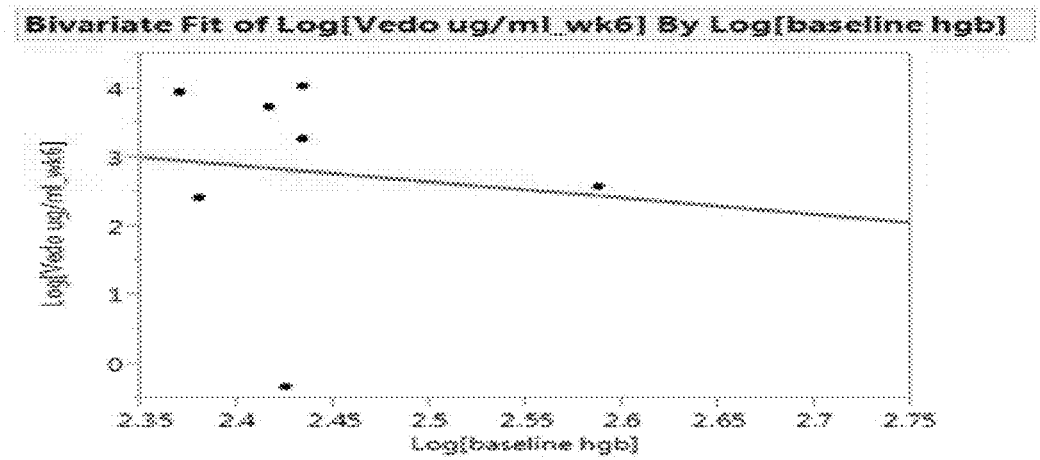
Figure 6A:
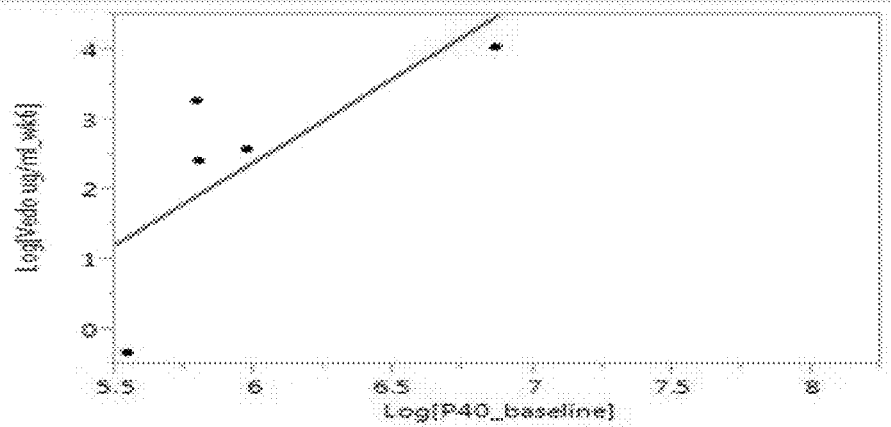
FIGS. 6A and 6B illustrate the relationship between either IL-12p40 or MMP9 and vedolizumab.
Figure 6B:
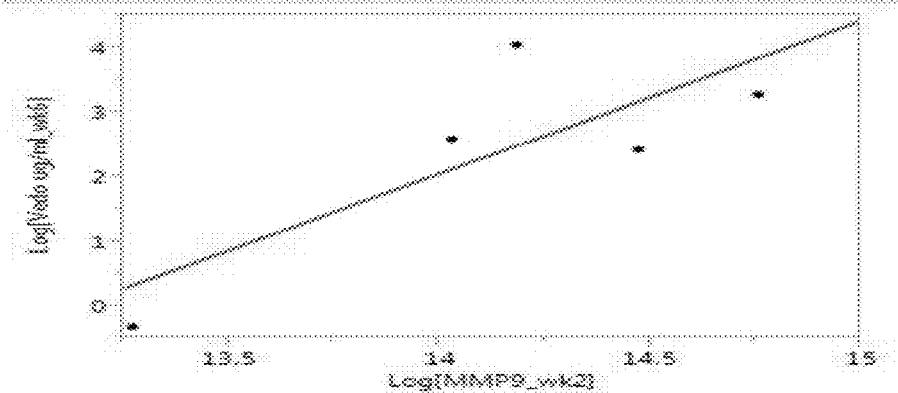
Figure 7A:
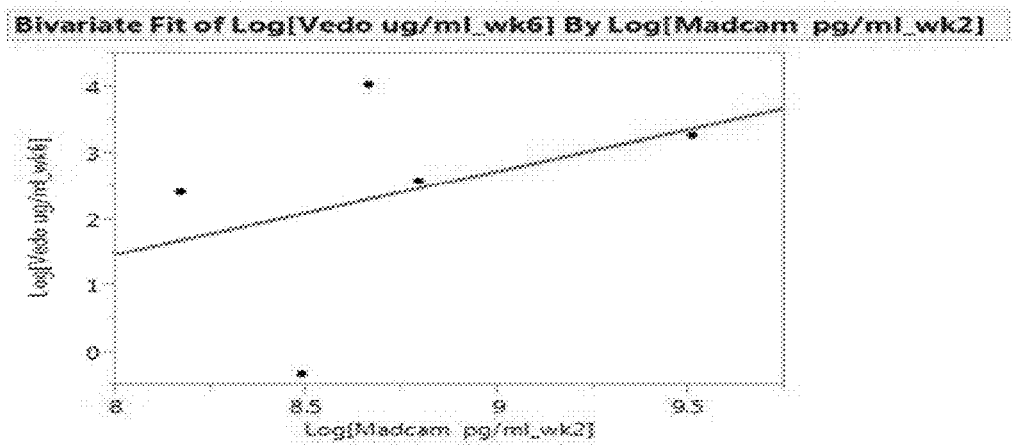
FIG. 7A shows a positive association between vedolizumab at week 6 and MAdCAM-1 at week 2.
Figure 7B:
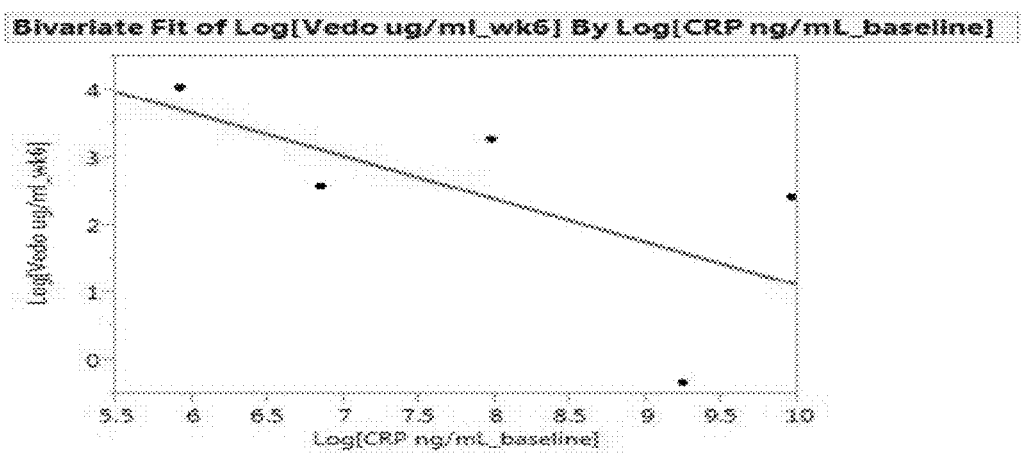
FIG. 7B shows an association between vedolizumab at week 6 and CRP at baseline.
Figure 8A:
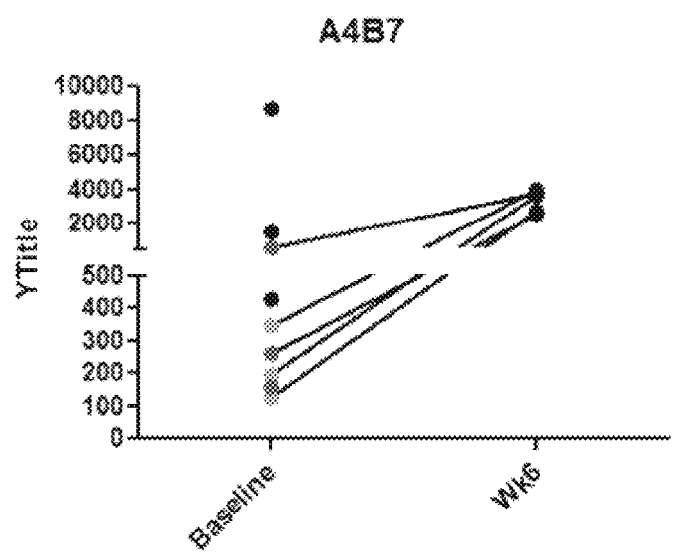
FIGS. 8A and 8B shows a diagram of an exemplary embodiment of the present invention that shows that treatment with vedolizumab result in increase in serum α4β7 integrin (FIG. 8A) and decrease in MAdCAM-1 (FIG. 8B) levels.
Figure 8B:
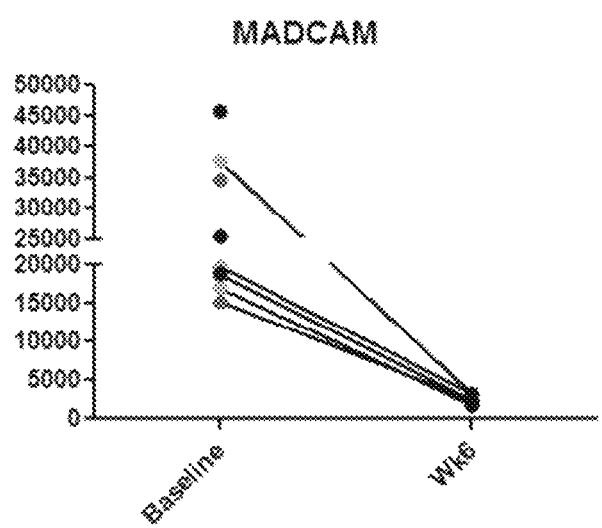
Figure 9:
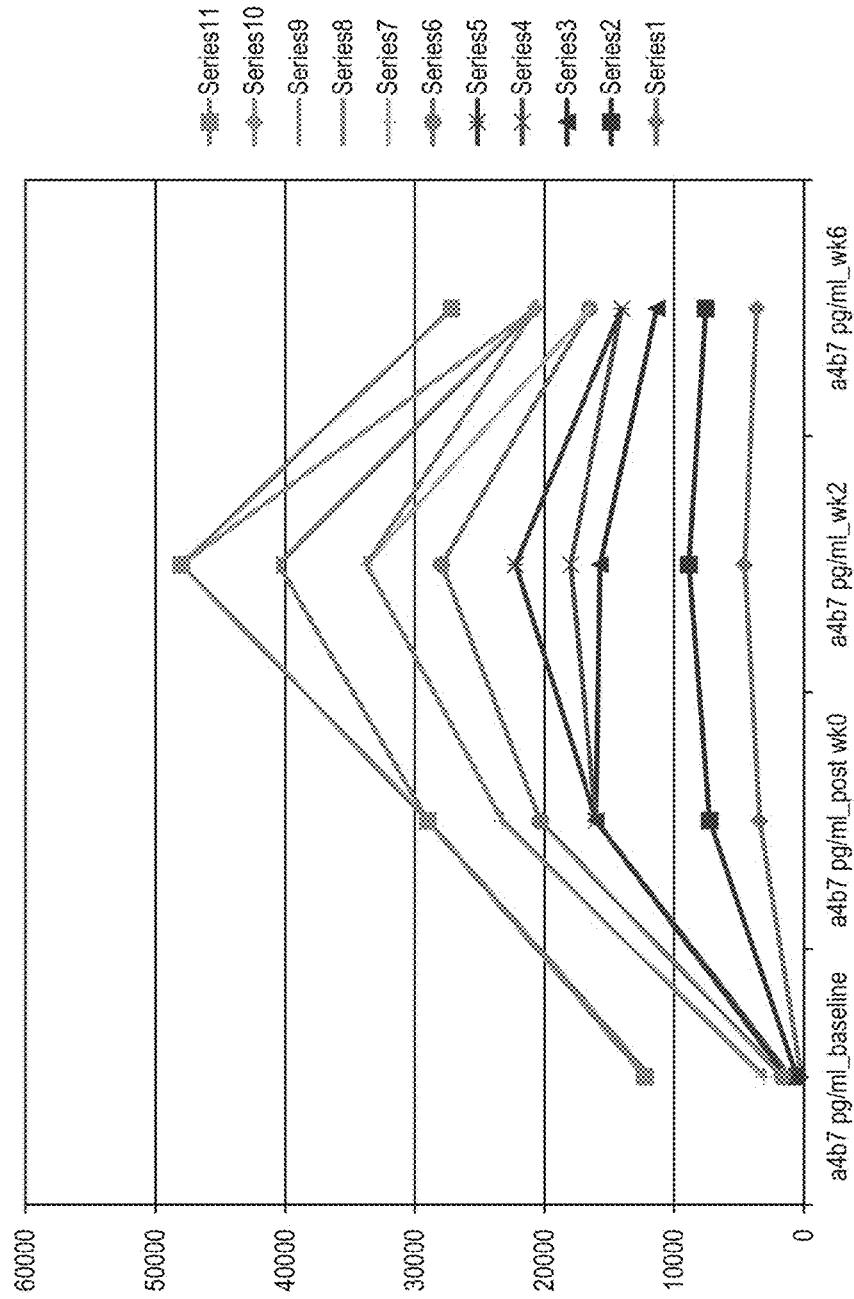
FIG. 9 shows the changes in serum α4β7 integrin levels during the course of vedolizumab therapy (e.g., at baseline, post week 0, week 2 and week 6) in samples tested.
Figure 10:
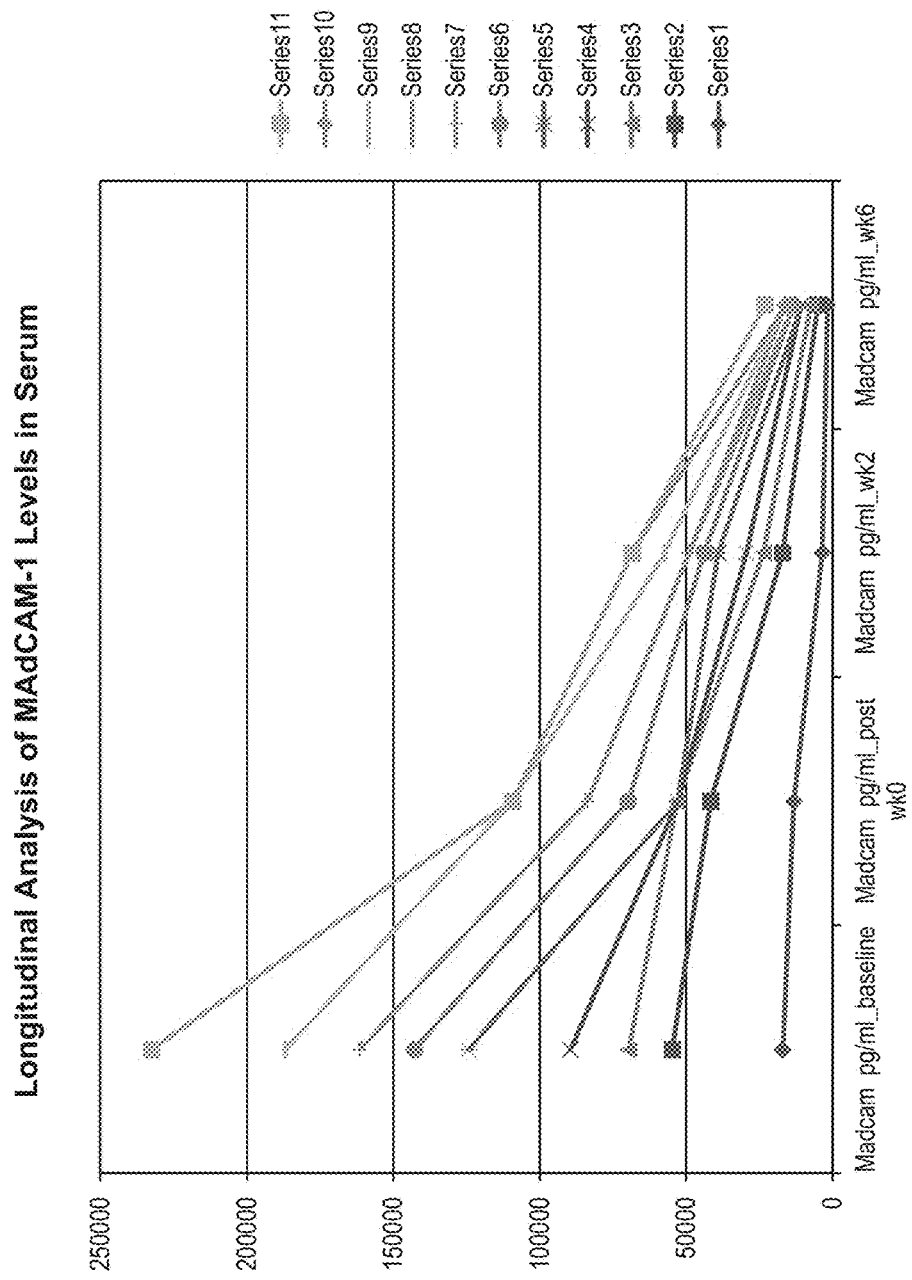
FIG. 10 shows a decrease in serum MAdCAM-1 levels during the course of vedolizumab therapy (e.g., at baseline, post week 0, week 2 and week 6) in samples tested.

Univariate regression analysis was performed to identify markers that can predict vedolizumab levels at week 6 of induction therapy. Baseline TNFα levels were higher in samples having lower levels of vedolizumab at week 6 (FIG. 1A). Also, TNFα levels at week 2 were higher in samples having lower vedolizumab levels at week 6 (FIG. 1B). VEGF levels at baseline were higher in samples having lower drug levels at week 6 (FIG. 2). Similarly, ANG-1 levels at baseline were higher in samples having higher vedolizumab levels at week 6 (FIG. 3B). Higher CRP levels at baseline were associated with lower drug levels at week 6 (FIG. 7B). ANG-2 levels at baseline were higher in samples having lower vedolizumab levels at week 6 (FIG. 3A). High ADA levels at baseline and at week 2 also resulted in higher drug levels at week 6 (FIGS. 4A and 4B). Higher human serum albumin levels at baseline were detected when vedolizumab levels were higher at week 6 (FIG. 5A). The data also showed a positive association between the anti-α4β7 integrin drug at week 6 and either IL-12p40 levels at baseline (FIG. 6A), MMP9 levels at week 2 (FIG. 6B) and MAdCAM-1 at week 2 (FIG. 7A). In other words, high levels of Il-12p40 at baseline correlated with high levels of vedolizumab at week 6. High levels of MMP9 at week 9 also correlated with high levels of drug at week 6. No such association was calculated for hemoglobin levels at baseline (FIG. 5B). Further analysis was performed to investigate the levels of α4β7 integrin or MAdCAM-1 relative drug levels during the course of treatment. Vedolizumab therapy increased serum α4β7 integrin (FIGS. 8A and 9) and decrease MAdCAM-1 levels (FIGS. 8B and 10) over time. A summary of the correlations between the markers tested is provided in Table 2.

TABLE 2

Summary of Correlations

| Marker 1 | Marker 2 | Correlation | P-value | Time point |
|---|---|---|---|---|
| ANG-1 | TNFα | −0.7183 | 0.0293 | Baseline |
| IL-12p40 | α4β7 integrin | 0.7262 | 0.0267 | Baseline |
| Tweak | CRP | 0.6847 | 0.0418 | Baseline |
| Tweak | TNFα | 0.7249 | 0.0271 | Baseline |
| ANG-2 | MMP9 | −0.7528 | 0.0192 | Baseline |
| CRP | Vedolizumab | −0.6849 | 0.0418 | Wk 2 |
| TNFa | CRP | 0.77 | 0.0152 | Wk 2 |
| MMP9 | ANG-1 | 0.806 | 0.0087 | Wk 2 |
| MMP9 | ICAM-1 | −0.7039 | 0.03 | Wk 2 |
| MMP9 | VCAM-1 | −0.7926 | 0.01 | Wk 2 |
| ANG-1 | ICAM-1 | −0.7022 | 0.0349 | Wk 2 |
| ANG-1 | VCAM-1 | −0.6453 | 0.06 (n.s.) | Wk 2 |
| ANG-1 | TNFα | −0.6727 | 0.047 | Wk 2 |

Figure 11A:
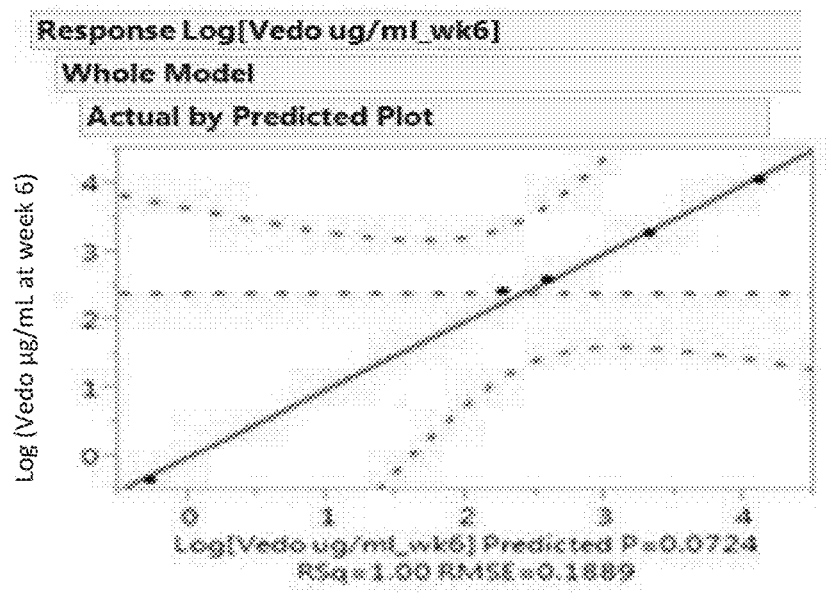
FIGS. 11A and 11B provide graphs of multiple regression models used to evaluate the correlations between two predictive biomarkers at baseline of vedolizumab treatment and levels of vedolizumab at week 6.
Figure 11B:
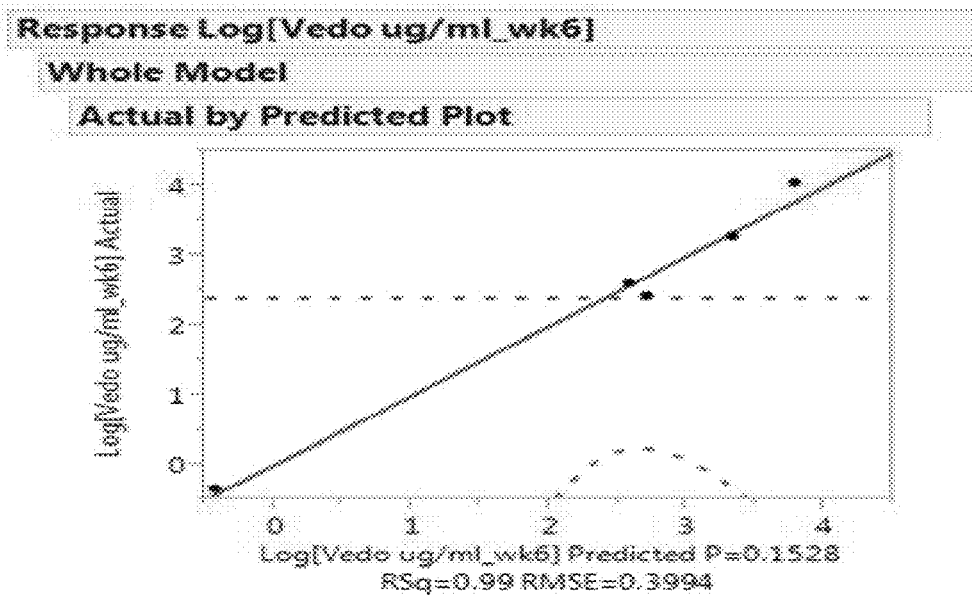

Using a multiple regression model it was determined that there is an interaction (correlation) between VCAM-1 and α4β7 integrin levels at baseline and a prediction of vedolizumab levels at week 6 (FIG. 11A). Further, an interaction between VCAM-1 and MadCAM-1 at baseline and a vedolizumab levels at week 6 was also established (FIG. 11B). The data suggested that the presence or level of one or more (e.g., 2, 3, 4, 5, 6, 7, 8, 9, 10 or more) markers at baseline (a first time point) can be used to predict drug levels at a future time point (a second time point) during the course of therapy. The results showed that VCAM-1 and α4β7 integrin levels at baseline can predict the presence of vedolizumab at week 6 and the absence of autoantibodies to the drug.

Figure 12A:
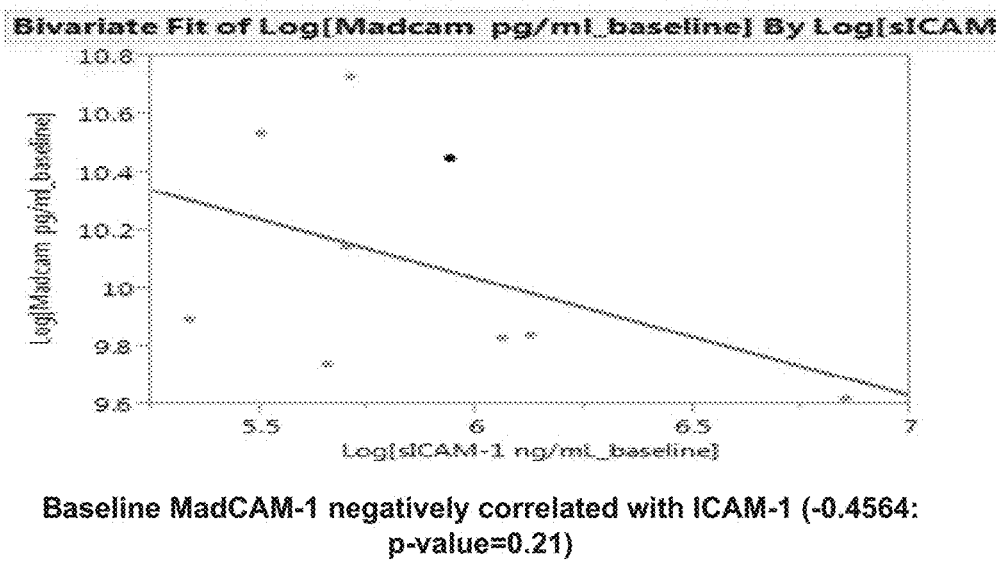
FIGS. 12A and 12B provide bivariate fit log graphs of MadCAM-1 levels versus ICAM-1 or VCAM-1.
Figure 12B:
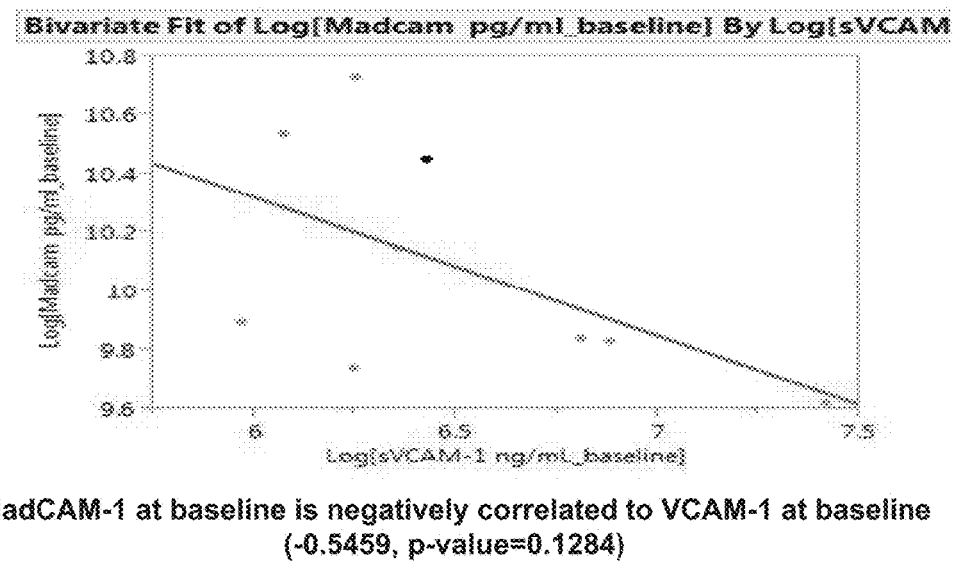

The results showed that MAdCAM-1 levels negatively correlated to ICAM-1 levels (FIG. 12A) and VCAM-1 levels (FIG. 12B).

Figure 13:
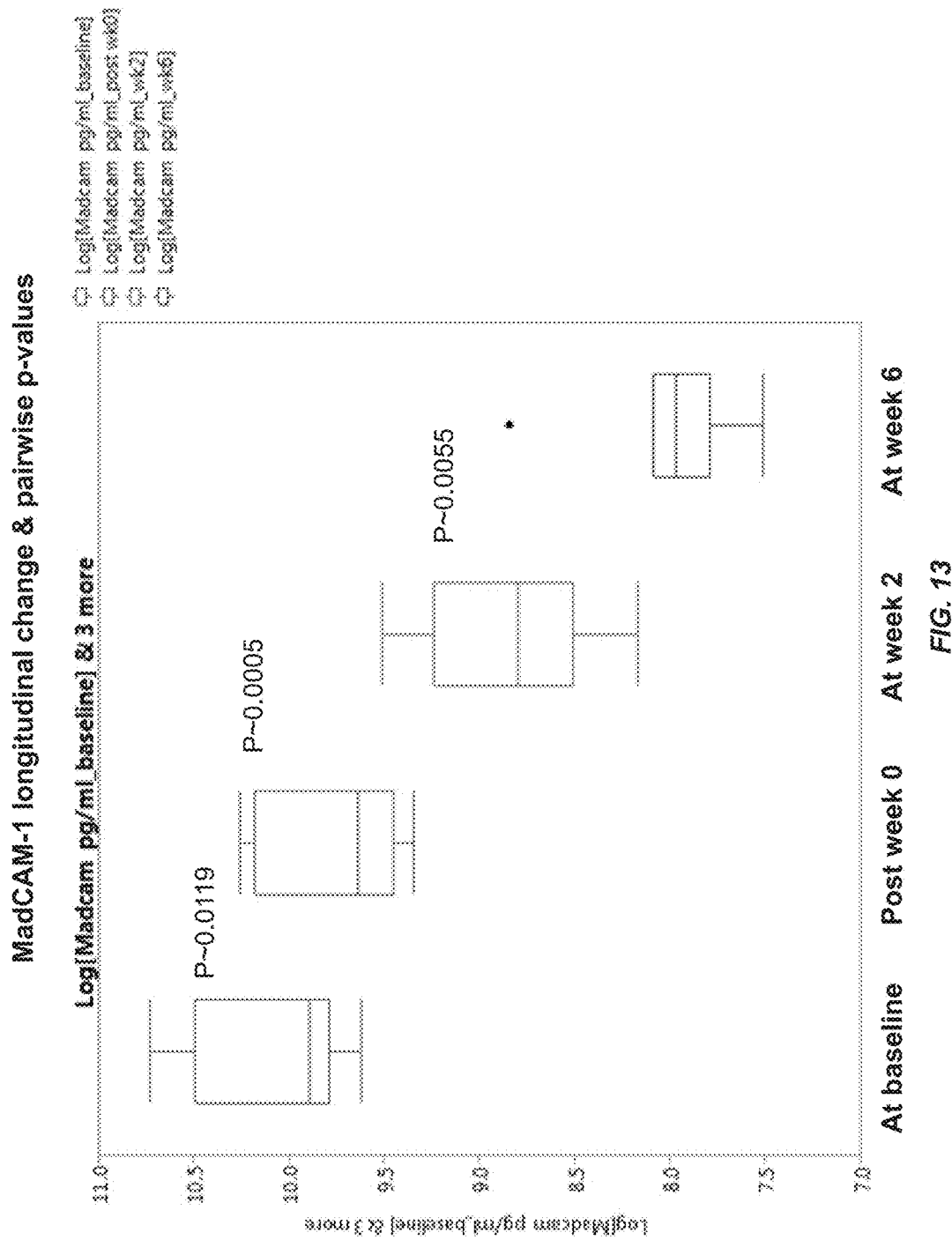
FIG. 13 shows the longitudinal change of MadCAM-1 levels during vedolizumab induction therapy and pairwise p-values.
Figure 14:
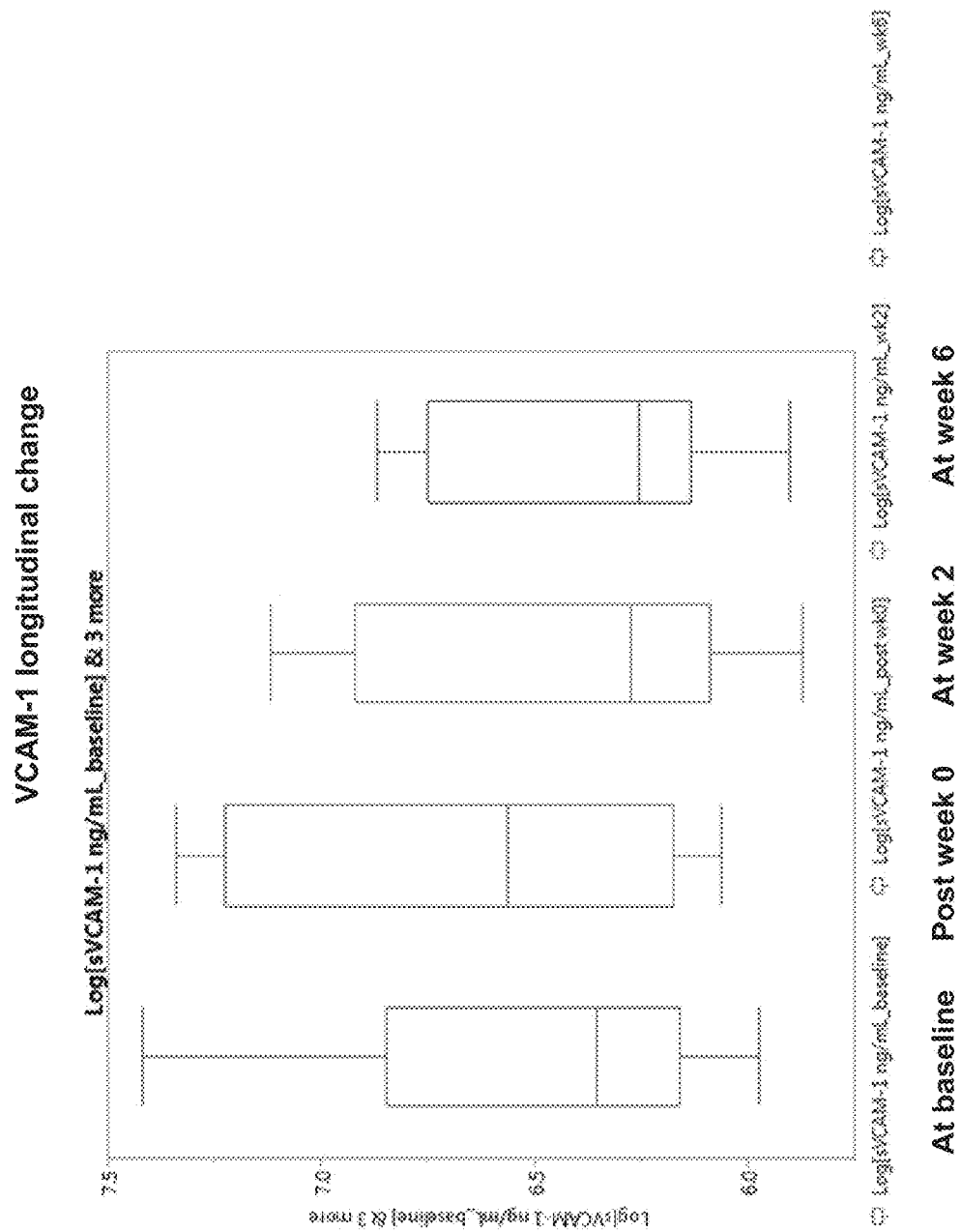
FIG. 14 shows no change of VCAM-1 levels during vedolizumab induction therapy.
Figure 15:
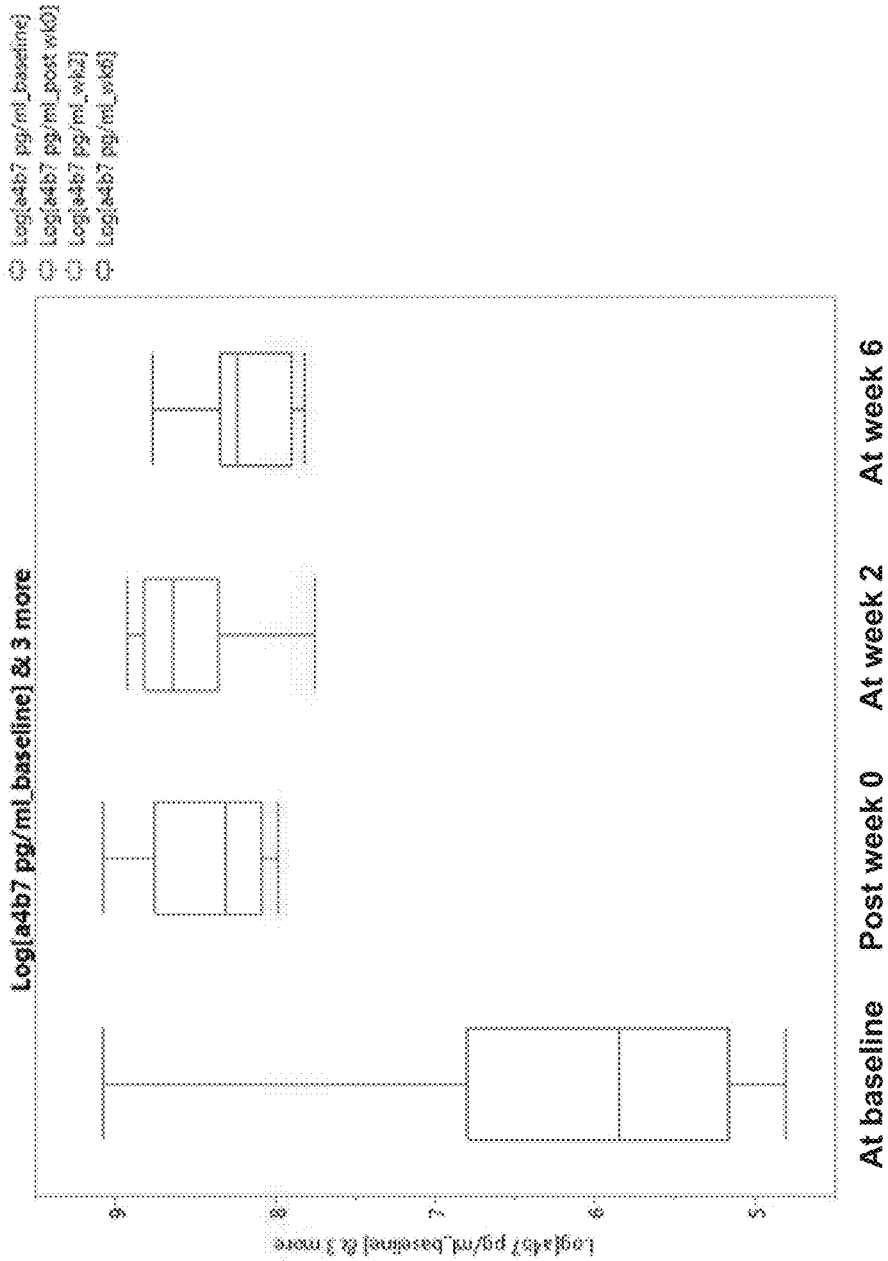
FIG. 15 shows the longitudinal change of serum α4β7 integrin levels during vedolizumab induction therapy.
Figure 16:
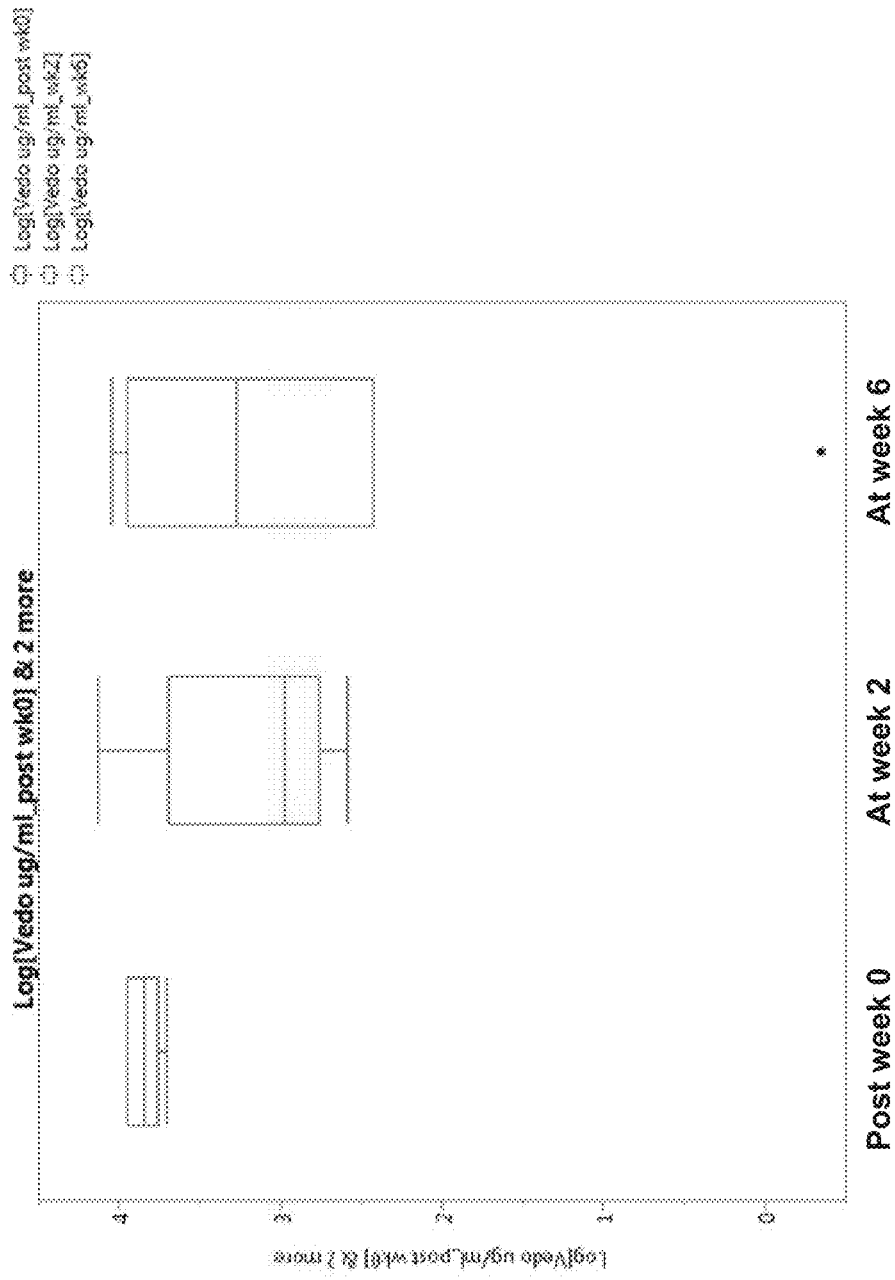
FIG. 16 shows stable levels of vedolizumab across induction therapy.
Figure 17:
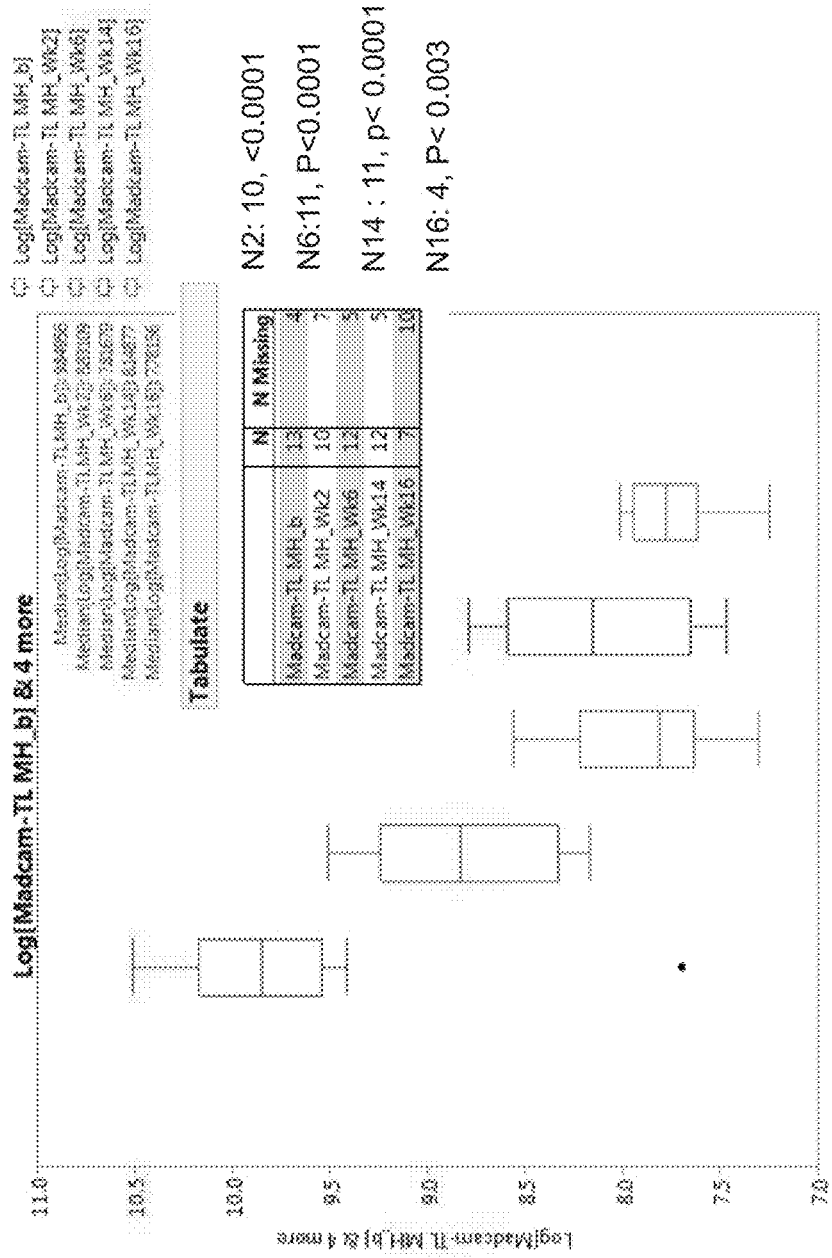
FIG. 17 shows the longitudinal change of MAdCAM-1 across visits in patients responding to vedolizumab. P-values are calculated for change from baseline for each visit from induction therapy through maintenance therapy. The differences are statistically significant.
Figure 18:
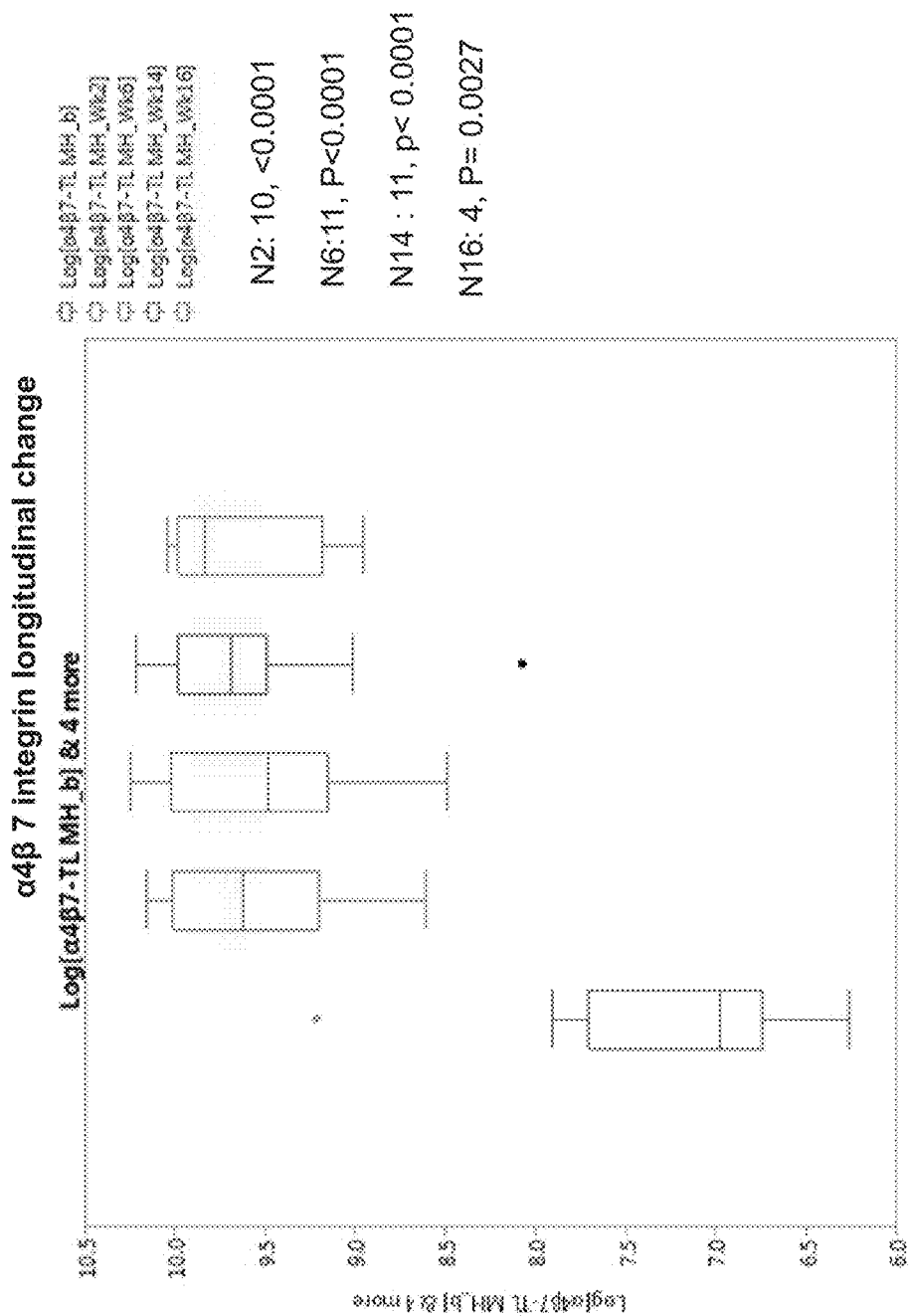
FIG. 18 shows the longitudinal change of serum α4β7 integrin across visits in patients responding to vedolizumab. P-values are calculated for change from baseline for each visit from induction therapy through maintenance therapy. The differences are statistically significant.

Longitudinal analyses (e.g., analysis at baseline, post-week 0, week 2 and week 6 of therapy) of marker levels and vedolizumab levels were performed. MAdCAM-1 levels decreased during the course of therapy at the initiation phase and induction phase (FIG. 13), and in the maintenance phase (FIG. 17). VCAM-1 levels did not change statistically significantly with time (FIG. 14). Serum α4β7 integrin levels were low at baseline and increased during induction therapy (FIG. 15) and remained high during maintenance therapy (FIG. 18). In these samples, vedolizumab levels were about the same during induction therapy (FIG. 16). The results of the analyses show that the patients did not develop autoantibodies against vedolizumab. The data shows that a decrease in MadCAM-1 levels and an increase in serum 4β7 integrin levels across induction therapy predicts that patient with CD or UC will likely have a clinical response to vedolizumab at week 6 of treatment. The patient is also likely to have clinical remission during maintenance therapy.

Figure 19A:
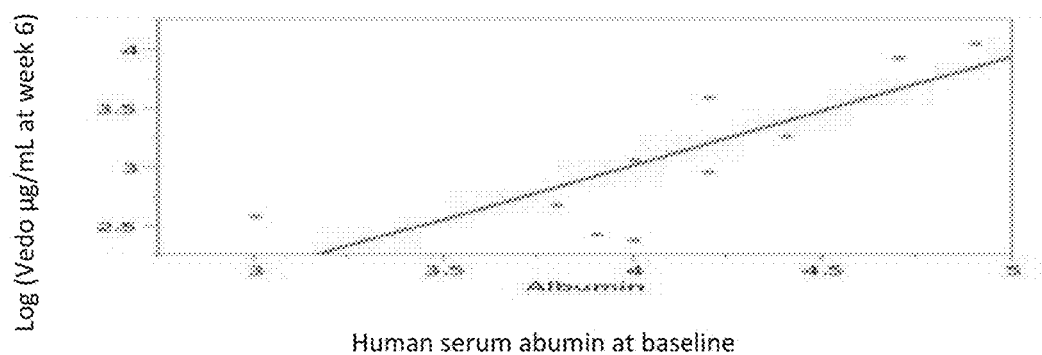
FIGS. 19A and 19B provide bivariate fit log graphs that compare serum albumin levels and vedolizumab levels.
Figure 19B:
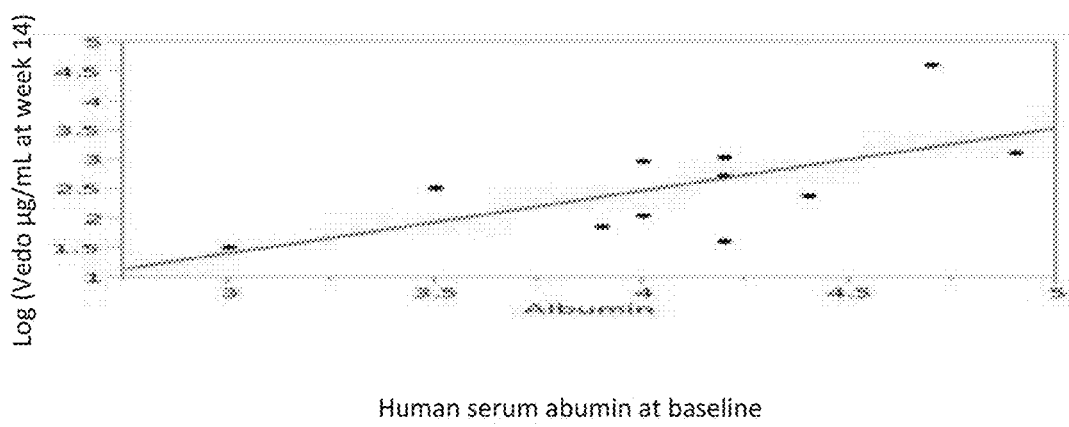
Figure 20A:
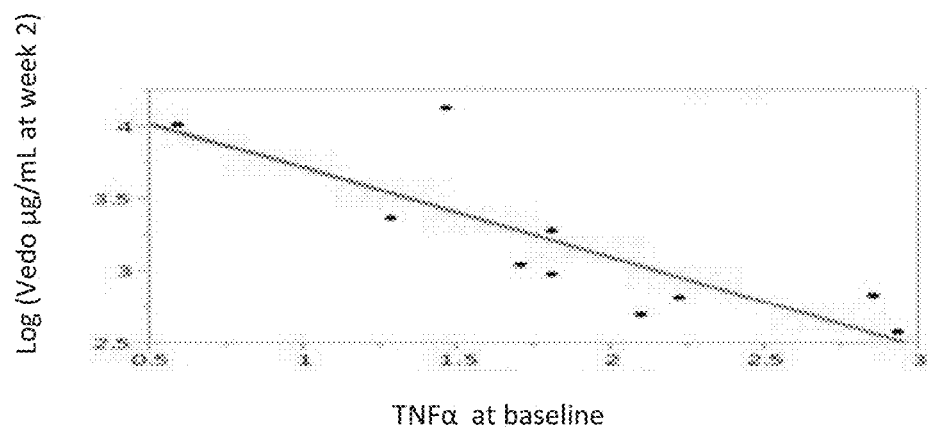
FIGS. 20A and 20B provide bivariate fit log graphs that compare TNFα levels and vedolizumab levels.
Figure 20B:
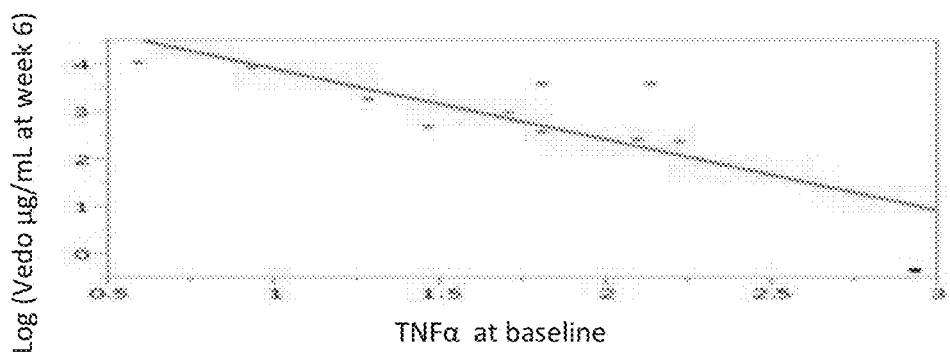

Further analysis revealed that there is a positive correlation between the levels of human serum albumin at baseline and levels of vedolizumab at week 6 (induction phase) and week 14 (maintenance phase) of treatment (FIGS. 19A and 19B). There was a negative correlation between the levels of TNFα at baseline and levels of vedolizumab at week 2 and week 6 of treatment (FIGS. 20A and 20B).

Table 3 provides data of the bivariate fit graphs that analyze vedolizumab vs. TNFα (FIGS. 1A and 1B), vedolizumab vs. VEGF (FIG. 2), vedolizumab vs. ANG-2 (FIG. 3A), and vedolizumab vs. ANG-1 (FIG. 3B).

TABLE 3

Summary of Bivariate Fit Graphs of Vedolizumab with TNFα, VEGF, ANG-2 and ANG-1

| | | log Vedo (ug/ml at wk 6) v. log TNFa (pg/ml at baseline) | log Vedo (ug/ml at wk 6) v. log TNFa (pg/ml at wk 2) | log Vedo (ug/ml at wk 6) v. log VEGF (pg/ml at baseline) | log Vedo (ug/ml at wk 6) v. log ANG-2 (pg/ml at baseline) | log Vedo (ug/ml at wk 6) v. log ANG-1 (pg/ml at baseline) |
|---|---|---|---|---|---|---|
| linear fit | | log Vedo (ug/ml at wk 6) = −5.5242934 − 1.7970711*[log TNFa (pg/ml at baseline)] | log Vedo (ug/ml at wk 6) = −4.3374543 − 1.8306673*[log TNFa (pg/ml at wk 2)] | log Vedo (ug/ml at wk 6) = 10.277741 − 1.424572*[log VEGF (pg/ml at baseline)] | log Vedo (ug/ml at wk 6) = 8.731798 − 09235765 *[log ANG-2 (pg/ml at baseline)] | log Vedo (ug/ml at wk 6) = −5.45025 + 5.179299 *[log ANG-1 (pg/ml at baseline)] |
| Rsquare | | 0.901884 | 0.882787 | 0.511011 | 0.501428 | 0.841118 |
| Rsquare Adj | | 0.869178 | 0.843715 | 0.348015 | 0.252148 | 0.788158 |
| Root Mean Square Error | | 0.600528 | 0.656373 | 1.340638 | 1.379359 | 0.764186 |
| Mean of Response | | 2.398325 | 2.398325 | 2.398325 | 1.986356 | 2.398325 |
| Observations (or Sum Weights) | | 5 | 5 | 5 | 4 | 5 |

TABLE 3-continued

Summary of Bivariate Fit Graphs of Vedolizumab with TNFα, VEGF, ANG-2 and ANG-1

|  | log Vedo (ug/ml at wk 6) v. log TNFa (pg/ml at baseline) | log Vedo (ug/ml at wk 6) v. log TNFa (pg/ml at wk 2) | log Vedo (ug/ml at wk 6) v. log VEGF (pg/ml at baseline) | log Vedo (ug/ml at wk 6) v. log ANG-2 (pg/ml at baseline) | log Vedo (ug/ml at wk 6) v. log ANG-1 (pg/ml at baseline) |
|---|---|---|---|---|---|
| Analysis of Variance (Model DF; Sum of Squares; Mean Square, F Ratio) | 1; 9.944800; 9.94480; 27.5759 | 1; 9.734222; 9.73422; 22.5943 | 1; 5.634768; 5.63477; 3.1351 | 1; 3.8270572; 3.82706; 2.0115 | 1; 9.274757; 927476; 15.8820 |
| Analysis of Variance (Error; DF; Sum of Squares; Mean Square, F Ratio) | 3; 1.081900; 0.36063; -- | 3; 1.292477; 0.43083; -- | 3; 5.391932; 1.79731; -- | 2; 3.8052615; 1.90263; --; -- | 3; 1.751943; 0.58398; -- |
| Analysis of Variance (C Total; DF; Sum of Squares; Mean Square, F Ratio) | 4; 11.026700; --; -- | 4; 11.026700; --; -- | 4; 11.026700; --; -- | 3; 7.6323188; -; - | 4; 11.026700; --; -- |
| Prob > F | 0.0134 | 0.0177 | 0.1748 | 0.2919 | 0.0283 |
| Parameter Estimate (Intercept; estimate std error; t ratio; Prob > [t]) | 5.5242934; 0.653056; 8.46; 0.0035 | 4.3374543; 0.502582; 8.63; 0.0033 | 10.27741; 4.490284; 2.29; 0.1061 | 8.7831798; 4.841747; 1.81; 0.2113 | -53.45025; 14.0181; -3.81; 0.0317 |
| Parameter Estimate (X-value; estimate std error; t ratio; Prob > [t]) | -1.797071, 0.342216, -5.25, 0.0134 | -1830667; 0.385132; -4.75; 0.0177 | -1.424572; 0.804559; -1.77; 0.1748 | -0.923576; 0.6581205; -1.42; 0.299 | 5.179299; 1.299628; 3.99; 0.0283 |
| Robust Fit (Sigma; chi square; P-value; LogWorth) | NA | NA | 1.41317; 6.55162; 0.01018; 1.97968 | 1.45399; 423246; 0.3966; 1.40167 | 0.80553; 53.843; 2.2e-13; 12.6632 |
| Parameter (Intercept; robust estimate; Std error) | NA | NA | 10.2777; 2.62271 | 8.78318; 2.87003 | -53.45; 7.42013 |
| Parameter (X-value; robust estimate; Std error) |  |  | -1.4246; 0.55656 | -0.9236; 0.44893 | 5.1793; 0.70584 |

Table 4 provides data of the bivariate fit graphs that analyze vedolizumab vs. ADA (FIGS. 4A and 4B), vedolizumab vs. albumin (FIG. 5A), and vedolizumab vs. hemoglobin (FIG. 5B).

TABLE 4

Summary of Bivariate Fit Graphs of Vedolizumab with ADA, Albumin and Hemoglobulin

|  |  | log Vedo (ug/ml at wk 6) v. log ADA (pg/ml atbaseline) | log Vedo (ug/ml at wk 6) v. log ADA (pg/ml at week 2) | log Vedo (ug/ml at wk 6) v. log albumin (pg/ml at baseline) | log Vedo (ug/ml at wk 6) v. log hemoglobin (pg/ml at baseline) |
|---|---|---|---|---|---|
| linear fit |  | log Vedo (ug/ml at wk 6) = -18.26969 + 2.8022482 log ADA (pg/ml at baseline) | log Vedo (ug/ml at wk 6) = -19.71982 + 3.0702953*[log ADA (pg/ml at week 2)] | log Vedo (ug/ml at wk 6) = -3.112497 + 4.5289224* [log albumin (pg/ml at baseline)] | log Vedo (ug/ml at wk 6) = 8.5923412 - 2.3740808* [log hemoglobin (pg/ml at baseline)] |
| Rsquare |  | 0.456554 | 0.799121 | 0.405153 | 0.12482 |
| Rsquare Adj |  | 0.275405 | 0.732161 | 0.286184 | -0.18502 |
| Root Mean Square Error |  | 1.41332 | 0.85927 | 1.292116 | 1.664837 |
| Mean of Response |  | 2.398325 | 2.398325 | 2.811286 | 2.811286 |
| Observations (or Sum Weights) |  | 5 | 5 | 7 | 7 |
| Analysis of Variance (Model DF; Sum of Squares; Mean Square, F Ratio) |  | 1; 5.034280; 5.03428; 2.5203 | 1; 8.811665; 8.1166; 11.9343 | 1; 5.685742; 5.68574; 3.4055 | 1; 0.175160; 0.17516; 0.0632 |

TABLE 4-continued

Summary of Bivariate Fit Graphs of Vedolizumab with ADA, Albumin and Hemoglobulin

|  | log Vedo (ug/ml at wk 6) v. log ADA (pg/ml atbaseline) | log Vedo (ug/ml at wk 6) v. log ADA (pg/ml at week 2) | log Vedo (ug/ml at wk 6) v. log albumin (pg/ml at baseline) | log Vedo (ug/ml at wk 6) v. log hemoglobin (pg/ml at baseline) |
|---|---|---|---|---|
| Analysis of Variance (Error; DF; Sum of Squares; Mean Square, F Ratio) | 3; 5.992419; 1.99747; --; -- | 3; 2.215035; 0.73835; -- | 5; 8.347823; 1.66956; -- | 5; 13.858404; 2.77168; -- |
| Analysis of Variance (C Total; DF; Sum of Squares; Mean Square, F Ratio) | 4; 11.026700; --; -- | 4; 11.026700; --; -- | 6; 14.033565; --; -- | 6; 14.033565; --; -- |
| Prob > F | 0.2106 | 0.0408 | 0.1243 | 0.8115 |
| Parameter Estimate (Intercept; estimate std error; t ratio; Prob > [t]) | −18.26969; 1303412; −1.40; 0.2556 | −19.71982; 6.414018; −3.07; 0.0544 | −3.112497; 3.246954; −0.96; 0.3818 | 8.5923412; 23.00505; 0.37; 0.7241 |
| Parameter Estimate (X-value; estimate std error; t ratio; Prob > [t]) | 2.8022482; 1765137; 1.59; 0.106 | 3.0702953; 0.88753; 3.45; 0.0408 | 4.5289224; 2.45416; 1.85; 0.1243 | −2.374081; 9.443849; −0.25; 0.8115 |
| Robust Fit (Sigma; chi square; P-value; LogWorth) | 1.48979; 508451; 0.02414; 1.61725 | 0.90576; 15.7548; 7.21e-5; 4.14204 | 1.36203; 5.51481; 0.01886; 1.72455 | 1.75491; 0.80918; 0.36836; 0.43372 |
| Parameter (Intercept; robust estimate; Std error) | −18.27; 9.44979 | −19.72; 5.58927 | −3.1152; 2.88796 | 8.59234; 6.7798 |
| Parameter (X-value; robust estimate; Std error) | 2.80225; 1.24274 | 3.0703; 0.77352 | 4.52892; 1.92854 | −2.3741; 2.63921 |

Table 5 provides data of the bivariate fit graphs that analyze vedolizumab vs. IL-12p40 (FIG. 6A), vedolizumab vs. MadCAM-1 at week 2 (FIG. 7A), vedolizumab vs. MMP9 at week 2 (FIG. 6B), MadCAM-1 vs. soluble ICAM-1 (FIG. 12A), and MadCAM-1 vs. soluble VCAM-1 (FIG. 12B).

TABLE 5

Summary of Bivariate Fit Graphs of Vedolizumab with IL-12p40, MadCAM-1, and MMP9, and MadCAM-1 with ICAM-1 and VCAM-1

|  |  | log Vedo (ug/ml at wk 6) v. log IL-12p40 (pg/ml at baseline) | log Vedo (ug/ml at wk 6) v. log MMP9 (pg/ml at wk 2) | log Vedo (ug/ml at wk 6) v. log MadCAM-1 (pg/ml at wk 2) | log MadCAM-1 (pg/ml at baseline) v. log sICAM-1 (ng/ml at baseline) | log MadCAM-1 (pg/ml at baseline) v. log sVCAM-1 at baseline) |
|---|---|---|---|---|---|---|
|  | linear fit | log Vedo (ug/ml at wk 6) = −11.88877 + 2.3841137 *[log IL-12p40 (pg/ml at baseline)] | log Vedo (ug/ml at wk 6) = −30.96904 + 2.3590076*[log MMP9 (pg/ml at week 2)] | log Vedo (ug/ml at wk 6) = −8.529237 + 1.2524517*[log MadCAM-1 (pg/ml at week 2)] | log MadCAM-1 (pg/ml at baseline) = 12.466926 − 0.40506*[log sICAM-1 (ng/ml at baseline)] | log MadCAM-1 (pg/ml at baseline) = 13.133267 − 0.4690828*[log sVCAM-1 (ng/mlat baseline)] |
|  | Rsquare | 0.538091 | 0.637475 | 0.140385 | 0.208307 | 0.29805 |
|  | Rsquare Adj | 0.384122 | 0.516633 | −0.14615 | 0.095208 | 0.197771 |
|  | Root Mean Square Error | 1.302988 | 1.154333 | 1.777519 | 0.376394 | 0.35442 |
|  | Mean of Response | 2.398325 | 2.398325 | 2.398325 | 10.08734 | 10.08734 |
|  | Observations (or Sum Weights) | 5 | 5 | 5 | 9 | 9 |
|  | Analysis of Variance (Model DF; Sum of Squares; Mean Square, F Ratio) | 1; 5.933370; 5.93337; 3.4948 | 1; 7.029242; 7.02924; 5.2753 | 1; 1.547979; 1.5498; 0.4899 | 1; 0.2609350; 0.260935; 1.8418 | 1; 0.3733504; 0.373350; 2.9722 |
|  | Analysis of Variance (Error; DF; Sum of Squares; Mean Square, F Ratio) | 3; 5.093330; 1.69778; -- | 3; 3.997457; 1.33249; -- | ; 9.478721; 3.15957; -- | 7; 0.9917089; 0.141673; -- | 7; 0.8792935; 0.125613; -- |

TABLE 5-continued

Summary of Bivariate Fit Graphs of Vedolizumab with IL-12p40, MadCAM-1, and MMP9, and MadCAM-1 with ICAM-1 and VCAM-1

|  | log Vedo (ug/ml at wk 6) v. log IL-12p40 (pg/ml at baseline) | log Vedo (ug/ml at wk 6) v. log MMP9 (pg/ml at wk 2) | log Vedo (ug/ml at wk 6) v. log MadCAM-1 (pg/ml at wk 2) | log MadCAM-1 (pg/ml at baseline) v. log sICAM-1 (ng/ml at baseline) | log MadCAM-1 (pg/ml at baseline) v. log sVCAM-1 at baseline) |
|---|---|---|---|---|---|
| Analysis of Variance (C Total; DF; Sum of Squares; Mean Square, F Ratio) | 4; 11.026700; --; -- | 4; 11.026700; --; -- | 4; 11.026700; --; -- | 8; 1.2526439; --; -- | 8; 1.2526439; --; -- |
| Prob > F | 0.1583 | 0.1053 | 0.5344 | 0.2169 | 0.1284 |
| Parameter Estimate (Intercept; estimate std error; t ratio; Prob > [t]) | -11.88877; 7.66465; -1.55; 0.2187 | -30.96904; 14.53694; -2.13; 0.1230 | -8.529237; 15.6321; -0.55; 0.6233 | 12.466926; 1.75787; 7.09; 0.0002 | 13.133267; 1.77071; 7.42; 0.0001 |
| Parameter Estimate (X-value; estimate std error; t ratio; Prob > [t]) | 2.3841137; 1.275312; 1.87; 0.1583 | 2.3590076; 1.027085; 2.30; 0.1503 | 1.2524517; 1.78947; 0.70; 0.5344 | -0.40506; 0.298467; -1.36; 0.2169 | -0.469083; 0.272088; -1.72; 0.1284 |
| Robust Fit (Sigma; chi square; P-value; LogWorth) | 1.37349; 7.84119; 0.00511; 2.29184 | 1.21679; 16.0954; 0.00006; 4.22018 | 1.87369; 2.94639; 0.08607; 1.06515 | 0.39676; 4.70911; 0.03; 1.52283 | 0.3736; 6.5995; 0.0102; 1.99137 |
| Parameter (Intercept; robust estimate; Std error) | -11.889; 5.44922 | -30.969; 8.31154 | -8.5292; 6.89747 | 12.4669; 1.17294 | 13.1333; 1.27585 |
| Parameter (X-value; robust estimate; Std error) | 2.38411; 0.8514 | 2.35901; 0.588 | 1.25245; 0.72965 | -0.4051; 0.18666 | -0.4691; 0.1826 |

Table 6 provides data of the bivariate fit graphs that analyze vedolizumab vs. CRP (FIG. 7B), vedolizumab vs. albumin (FIGS. 19A and 19B), and vedolizumab vs. TNFα (FIGS. 20A and 20B).

TABLE 6

Summary of Bivariate Fit Graphs of Vedolizumab with CRP, Albumin and TNFα.

|  | log Vedo (ug/ml at wk 6) v. log CRP (ng/ml at baseline) | log Vedo (ug/ml at wk 6) v. log albumin (ng/ml at baseline) | log Vedo (ug/ml at wk 14) v. log albumin (ng/ml at baseline) | log Vedo (ug/ml at wk 2) v. log TNFa (pg/ml at baseline) | log Vedo (ug/ml at wk 6) v. log TNFa (pg/ml at baseline) |
|---|---|---|---|---|---|
| linear fit | log Vedo (ug/ml at week 6) =7.4766583 - 0.6358414*[log CRP (ng/ml at baseline)] | log Vedo (ug/ml at week 6) = -0.652687 + 0.9211269*[log albumin (ng/ml at baseline)] | log Vedo (ug/ml at week 14) = -1.769356 + 1.0637125*[log albumin (ng/ml at baseline)] | log Vedo (ug/ml at week 2) = 4.3372739 - 0.6198702*[log TNFa (np/ml at baseline)] | log Vedo (ug/ml at week 6) = 5.3935304 - 1.4873362*[log TNFa (np/ml at baseline)] |
| Rsquare | 0.404505 | 0.596686 | 0.40339 | 0.668319 | 0.636842 |
| Rsquare Adj | 0.206007 | 0.551873 | 0.3371 | 0.626859 | 0.596491 |
| Root Mean Square Error | 1.479453 | 0.397241 | 0.714957 | 0.325704 | 0.767368 |
| Mean of Response | 2.398325 | 3.140682 | 2.582196 | 3.176041 | 2.831056 |
| Observations (or Sum Weights) | 5 | 11 | 11 | 10 | 11 |
| Analysis of Variance (Model DF; Sum of Squares; Mean Square, F Ratio) | 1; 4.460357; 4.46036; 2.0378 | 1; 2.1011322; 2.10113; 13.3151 | 1; 3.1105533; 3.11055; 6.0852 | 1; 1.7100103; 1.71001; 16.1196 | 1; 9.293624; 9.29362; 15.7826 |
| Analysis of Variance (Error; DF; Sum of Squares; Mean Square, F Ratio) | 3; 6.566343; 2.18878; -- | 9; 1.4202036; 0.15780; -- | 9; 4.6004780; 0.51116; -- | 8; 0.8486634; 0.10608; -- | 9; 5.299677; 0.58885; -- |

TABLE 6-continued

Summary of Bivariate Fit Graphs of Vedolizumab with CRP, Albumin and TNFα.

| | log Vedo (ug/ml at wk 6) v. log CRP (ng/ml at baseline) | log Vedo (ug/ml at wk 6) v. log albumin (ng/ml at baseline) | log Vedo (ug/ml at wk 14) v. log albumin (ng/ml at baseline) | log Vedo (ug/ml at wk 2) v. log TNFa (pg/ml at baseline) | log Vedo (ug/ml at wk 6) v. log TNFa (pg/ml at baseline) |
|---|---|---|---|---|---|
| Analysis of Variance (C Total; DF; Sum of Squares; Mean Square, F Ratio) | 4; 11.026700; --; -- | 10; 3.5213359; --; -- | 10; 7.7110313; --; -- | 9; 2.5586737; --; -- | 10; 14.593301; --; -- |
| Prob > F | 0.2487 | 0.0053 | 0.0358 | 0.0039 | 0.0032 |
| Parameter Estimate (Intercept; estimate std error; t ratio; Prob > [t]) | 7.466583; 3.618443; 2.07; 0.1307 | −0.652687; 1.046444; −0.62; 0.5483 | −1.769356; 1.777151; −1.00; 0.3455 | 4.3372739; 0.307021; 14.13; <0.0001 | 5.3935304; 0.685257; 7.87; <0.0001 |
| Parameter Estimate (X-value; estimate std error; t ratio; Prob > [t]) | −0.635841; 0.445415; −1.43; 0.2487 | 0.9211269; 0.252433; 3.65; 0.0053 | 1.0637125; 0.431207; 2.47; 0.358 | −0.61987; 0.154392; −4.01; m0.0039 | −1.487336; 0.374386; −3.97; |
| Robust Fit (Sigma; chi square; P-value; LogWorth) | 1.5595; 3.74565; 0.05295; 1.27617 | 0.41873; 14.5684; 0.00014; 3.86915 | 0.75364; 8.92485; 0.00281; 2.55081 | 0.33085; 18.2345; 0.00002; 4.70927 | 0.80889; 11.3313; 0.00076; 3.11798 |
| Parameter (Intercept; robust estimate; Std error) | 7.47555; 2.23707 | −0.6527; 1.04094 | −1.7694; 1.35522 | 4.32507; 0.39341 | 5.39353; 0.64127 |
| Parameter (X-value; robust estimate; Std error) | −0.6358; 0.3254 | 0.92113; 0.24133 | 1.06371; 0.35606 | −0.6157; 0.14419 | −1.4873; 0.44184 |

Table 7 provides data of the multivariate regression analysis of vedolizumab levels at week 6 in association with either (a) αβ integrin at baseline and soluble VCAM-1 at baseline (FIG. 11A), or (b) soluble VCAM-1 at baseline and MadCAM-1 at baseline (FIG. 11B).

TABLE 7

Summary of Multivariate Regression Models with Interactions between VCAM-1 and αβ Integrin or VCAM-1 and MadCAM-1 for Predicting Vedolizumab Levels at Week 6
Log [Vedo ug/ml at week 6] vs. Log [Vedo ug/ml at week 6]

| | |
|---|---|
| Predicted P | 0.0724 |
| R Square | 0.996763 |
| R Square Adj | 0.987054 |
| Root Mean Square Error | 0.188915 |
| Mean of Response | 2.398325 |
| Observations (Sum Wgts) | 5 |
| Model (DF; Sum of Squares; Mean Square; F Ratio) | 3; 10.991011; 3.66367; 102.6559 |
| Error (DF; Sum of Squares; Mean Square; F Ratio) | 1; 0.035689; 0.3569; -- |
| C. Total (DF; Sum of Squares; Mean Square; F Ratio) | 4; 11.026700; --; -- |
| Prob > F | 0.0724 |
| Intercept (Estimate; Std Error; t ratio; Prob > [t]) | 17.211202; 1.145423; 15.03; 0.423 |
| Log [sVCAM-1 ng/ml at baseline) (Estimate; Std Error; t ratio; Prob > [t]) | −4.392047; 0.277274; −15.84; 0.0401 |
| Log [a4b7 integrin pg/ml at baseline) (Estimate; Std Error; t ratio; Prob > [t]) | 0.2952687; 0.261342; 8.78; 0.722 |
| Log [sVCAM-1 ng/ml at baseline) −6.51781)*(Log [a4b7 pg/ml at baseline] −5.55963) (Estimate; Std Error; t ratio; Prob > [t]) | 5.0931735; 0.354773; 14.36; 0.0443 |
| Predicted P | 0.1528 |
| Rsquare | 0.985532 |
| Rsquare Adj | 0.942127 |
| Root Mean Square Error | 0.399423 |
| Mean of Response | 2.398325 |
| Observations (Sum Wgts) | 5 |

TABLE 7-continued

Summary of Multivariate Regression Models with Interactions between VCAM-1 and αβ Integrin or VCAM-1 and MadCAM-1 for Predicting Vedolizumab Levels at Week 6
Log [Vedo ug/ml at week 6] vs. Log [Vedo ug/ml at week 6]

| | |
|---|---|
| Model (DF; Sum of Squares; Mean Square; F Ratio) | 3; 10.867161; 3.62239; 22.7054 |
| Error (DF; Sum of Squares; Mean Square; F Ratio) | 1; 0.159538; 0.15954; -- |
| C. Total (DF; Sum of Squares; Mean Square; F Ratio) | 4; 11.026700; --; -- |
| Prob > F | 0.1528 |
| Intercept (Estimate; Std Error; t ratio; Prob > [t]) | 125.73107; 18.19193; 6.91; 0.0915 |
| Log [sVCAM-1 ng/ml at baseline) (Estimate; Std Error; t ratio; Prob > [t]) | −6.301264; 0.798176; −7.89; 0.0802 |
| Log [MadCAM-1 pg/ml at baseline) (Estimate; Std Error; t ratio; Prob > [t]) | −8.489875; 1.37403; −6.18; 0.1021 |
| Log [sVCAM-1 ng/ml at baseline] −6.51781)*(Log[MadCAM-1 pg/ml at baseline] −9.92376) (Estimate; Std Error; t ratio; Prob > [t]) | −19.3602; 2.753055; −7.03; 0.0899 |

Figure 21:
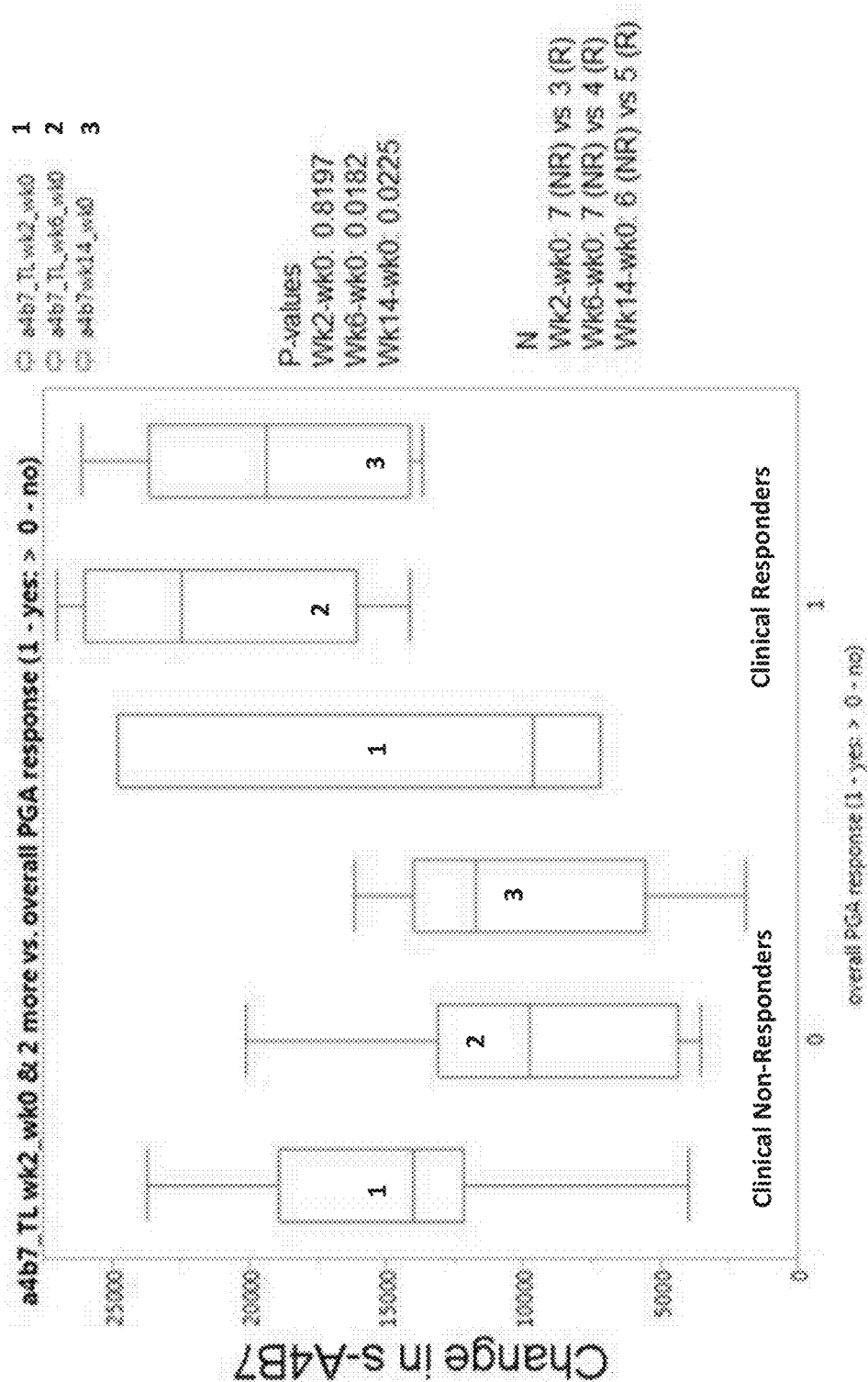
FIG. 21 provides a graph of the changes in s-α4β7 integrin levels between clinical responders of vedolizumab and non-responders, as determined by the Physician's Global Assessment (PGA). The graph shows changes in the levels from week 0 (baseline) to week 2 ("1"), from week 0 to week 6 ("2") and from week 0 to week 14 ("3") of vedolizumab treatment in clinical responder or non-responders. The change in s-α4β7 integrin levels was determined by subtracting the level at the earlier time point from the level at the later time point. The patients in this study were administered standard induction therapy and maintenance therapy of vedolizumab.

Additional analysis of responders to vedolizumab and levels of α4β7 integrin showed that patients who had a clinical response as based on Physician's Global Assessment (PGA) had a greater change or increase in α4β7 integrin levels compared to patient who were non-responders. FIG. 21 shows increases between levels at week 0 and week 2 (bars labeled "1") at week 0 and week 6 (bars labeled "2") and at week 0 and week 14 (bars labeled "3"). The differences in the increased levels between responders and non-responders were statistically significant when comparing those at week 0 to week 6 ("2") and at week 0 to week 14 ("3").

Figure 22:
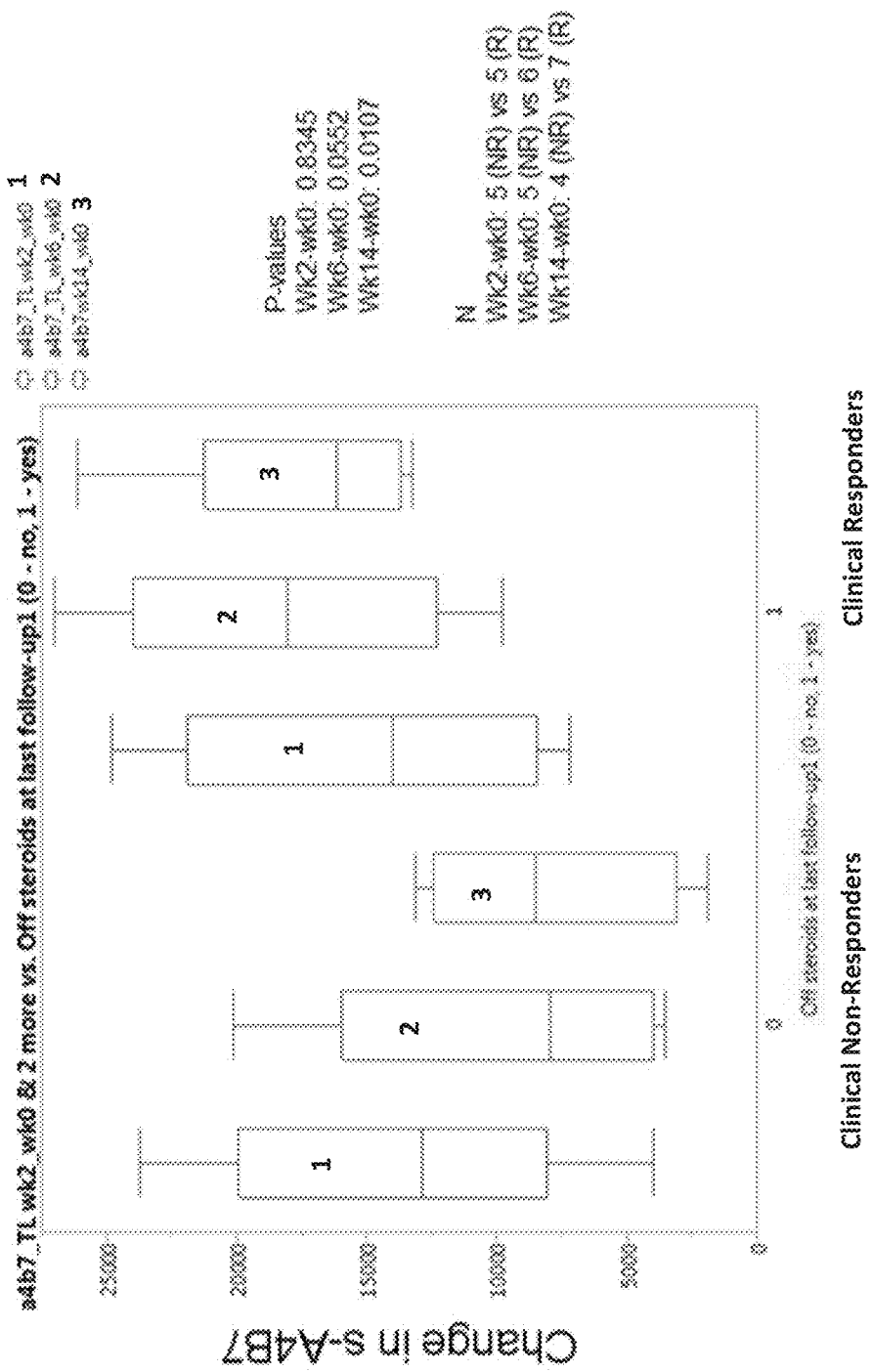
FIG. 22 provides a graph of the changes in s-α4β7 integrin levels between clinical responders of vedolizumab and non-responders, as determined by the withdrawal of steroid therapy. The graph shows changes in the levels from week 0 (baseline) to week 2 ("1"), from week 0 to week 6 ("2") and from week 0 to week 14 ("3") of vedolizumab treatment in clinical responder or non-responders. The change in s-α4β7 integrin levels was determined by subtracting the level at the earlier time point from the level at the later time point.

The correlation between clinical responders and increases in α4β7 integrin levels was also found when clinical response was defined as withdrawal from steroid therapy. FIG. 22 shows that clinical responders had a greater or larger increase in α4β7 integrin levels when changes between week 0 and week 14 were calculated. The difference between the responders and non-responders was statistically significant between the increased level at week 0 and the increased level at week 14 (p-value=0.0107). As such, s-α4β7 integrin level increases in the presence of vedolizumab treatment appear to be high in clinical responders than non-responders, based on PGA and withdrawal from steroid therapy. Changes in baseline of s-α4β7 integrin can serve as an effective biomarker for responsiveness to vedolizumab.

In summary, one or more markers, such as TNFα, human serum albumin (HSA), VEGF, angiopoietin-1 (ANG-1), angiopoietin-2 (ANG-2), adenosine deaminase (ADA), α4β7 integrin (α4β7), MAdCAM-1, hemoglobin (Hgb), C-reactive protein (CRP), matrix metalloproteinase 9 (MMP9), VCAM-1, and ICAM-1, can be used to predict response to therapy in patients treated with vedolizumab.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A therapy regimen for an anti-α4β7 integrin drug, wherein the anti-α4β7 integrin drug is ENTYVIO® (vedolizumab), said therapy regimen comprising:
measuring the presence or level of at least two predictive markers of MAdCAM-1, and VCAM-1 and optionally, a marker selected from the group consisting of TNFα, human serum albumin (HSA), VEGF, angiopoietin-1 (ANG-1), angiopoietin-2 (ANG-2), adenosine deaminase (ADA), serum α4β7 integrin, IL-12p40, C-reactive protein (CRP), MMP9, ICAM-1, and a combination thereof in a sample from a subject suffering from inflammatory bowel disease (IBD); and
administering the therapy regimen of the anti-α4β7 integrin drug, wherein the anti-α4β7 integrin drug is ENTYVIO® (vedolizumab), to the subject according to a predictive marker profile based on a lower level of the at least two predictive markers compared to a corresponding reference value, which reference value is the mean concentration of said markers in patients with IBD prior to initiation of vedolizumab, otherwise, administering an alternative therapy for IBD to said subject or maintaining an existing IBD therapy.

2. The therapy regimen of claim 1, wherein the subject is administered vedolizumab if the level of MadCAM-1, and VCAM-1 is lower than the corresponding reference value.

3. The therapy regimen of claim 1, further comprising measuring the level of TNFα, VEGF, ANG-2, and CRP, and administering an alternate therapy for IBD if the level of TNFα, VEGF, ANG-2, CRP, and/or VCAM-1 is higher than the corresponding reference value.

4. The therapy regimen of claim 1, wherein the sample is selected from the group consisting of a whole blood, serum or plasma sample.

5. The therapy regimen of claim 1, wherein the subject has had an inadequate response with, has lost response to, or was intolerant to an anti-TNFα drug.

6. The therapy regimen of claim 5 wherein the anti-TNFα drug is a member selected from the group consisting of REMICADE® (infliximab), ENBREL® (etanercept), HUMIRA® (adalimumab), CIMZIA® (certolizumab pegol), SIMPONI® (golimumab), STELARA® (ustekinumab), and combinations thereof.

7. The therapy regimen of claim 1, wherein the subject has not previously been administered the anti-α4β7 integrin drug.

8. The therapy regimen of claim 1, wherein the method further comprising applying a statistical analysis to the predictive marker profile to predict whether the subject will develop autoantibodies against the anti-α4β7 integrin drug.

9. The therapy regimen of claim 1, wherein the inflammatory bowel disease is ulcerative colitis (UC) or Crohn's Disease (CD).

* * * * *